United States Patent
Arnold et al.

(10) Patent No.: US 8,894,985 B2
(45) Date of Patent: *Nov. 25, 2014

(54) NITRIC OXIDE-RELEASING POLYMERS

(75) Inventors: Ernst V. Arnold, Hagerstown, MD (US);
Blaine G. Doletski, Elkridge, MD (US);
Robert E. Raulli, Manassas, VA (US)

(73) Assignee: Amulet Pharmaceuticals, Inc.,
Baltimore, MD (US)

( * ) Notice: Subject to any disclaimer, the term of this patent is extended or adjusted under 35 U.S.C. 154(b) by 825 days.

This patent is subject to a terminal disclaimer.

(21) Appl. No.: 12/940,208

(22) Filed: Nov. 5, 2010

(65) Prior Publication Data

US 2011/0059036 A1 Mar. 10, 2011

Related U.S. Application Data

(63) Continuation of application No. 10/588,718, filed as application No. PCT/US2005/000174 on Jan. 6, 2005, now Pat. No. 7,829,553.

(60) Provisional application No. 60/542,277, filed on Feb. 9, 2004.

(51) Int. Cl.
| | |
|---|---|
| *A61P 9/08* | (2006.01) |
| *C08G 63/685* | (2006.01) |
| *A61K 31/655* | (2006.01) |
| *A61L 31/10* | (2006.01) |
| *A61L 29/08* | (2006.01) |
| *A61L 27/34* | (2006.01) |
| *C08G 64/12* | (2006.01) |
| *C08F 8/30* | (2006.01) |

(52) U.S. Cl.
CPC .............. *C08F 8/30* (2013.01); *C08G 63/6854* (2013.01); *A61K 31/655* (2013.01); *A61L 31/10* (2013.01); *A61L 29/085* (2013.01); *A61L 27/34* (2013.01); *C08G 64/12* (2013.01)

USPC ....................................... 424/78.01

(58) Field of Classification Search
None
See application file for complete search history.

(56) References Cited

U.S. PATENT DOCUMENTS

| | | |
|---|---|---|
| 2,635,978 A | 4/1953 | Massengale |
| 2,954,314 A | 9/1960 | Metzger et al. |

(Continued)

FOREIGN PATENT DOCUMENTS

| | | |
|---|---|---|
| EP | 1300424 A1 | 4/2003 |
| WO | WO 95/12394 | 5/1995 |

(Continued)

OTHER PUBLICATIONS

Ahmade et al., "Suberimidate Crosslinking Shows that a Rod-shaped, Low Cystine, High Helix Protein Prepared by Limited Proteolysis of Reduced Wool has Four Protein Chains," *FEBS Letters*, Oct. 1978, vol. 94, No. 2, pp. 365-367, Elsevier/North-Holland Biomedical Press.

(Continued)

*Primary Examiner* — Brian Gulledge
(74) *Attorney, Agent, or Firm* — Foley & Lardner LLP

(57) ABSTRACT

This invention relates to compositions comprising carbon-based diazeniumdiolates attached to hydrophobic polymers that releases nitric oxide (NO). The carbon-based diazeniumdiolated polymers release NO spontaneously under physiological conditions without subsequence nitrosamine formation. The present invention also relates to methods of preparing the carbon-based diazeniumdiolated polymers, compositions comprising such polymers, methods of using such compositions, and devices employing such polymer compositions.

20 Claims, 3 Drawing Sheets

(56) References Cited

U.S. PATENT DOCUMENTS

| | | | |
|---|---|---|---|
| 3,309,373 A | 3/1967 | Danzig | |
| 4,954,526 A | 9/1990 | Keefer | |
| 5,039,705 A | 8/1991 | Keefer et al. | |
| 5,155,137 A | 10/1992 | Keefer et al. | |
| 5,208,233 A | 5/1993 | Keefer et al. | |
| 5,212,204 A | 5/1993 | Keefer et al. | |
| 5,250,550 A | 10/1993 | Keefer et al. | |
| 5,366,997 A | 11/1994 | Keefer et al. | |
| 5,374,710 A | 12/1994 | Tsien et al. | |
| 5,389,675 A | 2/1995 | Christodoulou et al. | |
| 5,405,919 A | 4/1995 | Keefer et al. | |
| 5,482,925 A | 1/1996 | Hutsell | |
| 5,519,020 A | 5/1996 | Smith et al. | |
| 5,525,357 A | 6/1996 | Keefer et al. | |
| 5,536,723 A | 7/1996 | Loscalzo et al. | |
| 5,574,068 A | 11/1996 | Stamler et al. | |
| 5,632,981 A | 5/1997 | Saavedra et al. | |
| 5,650,442 A | 7/1997 | Mitchell et al. | |
| 5,650,447 A | 7/1997 | Keefer et al. | |
| 5,665,077 A | 9/1997 | Rosen et al. | |
| 5,676,963 A | 10/1997 | Keefer et al. | |
| 5,683,668 A | 11/1997 | Hrabie et al. | |
| 5,691,423 A | 11/1997 | Smith et al. | |
| 5,698,738 A | 12/1997 | Garfield et al. | |
| 5,700,830 A | 12/1997 | Korthuis et al. | |
| 5,714,511 A | 2/1998 | Saavedra et al. | |
| 5,718,892 A | 2/1998 | Keefer et al. | |
| 5,721,365 A | 2/1998 | Keefer et al. | |
| 5,731,305 A | 3/1998 | Keefer et al. | |
| 5,770,645 A | 6/1998 | Stamler et al. | |
| 5,789,447 A | 8/1998 | Wink, Jr. et al. | |
| 5,811,121 A | 9/1998 | Wu et al. | |
| 5,814,656 A | 9/1998 | Saavedra et al. | |
| 5,814,666 A | 9/1998 | Green et al. | |
| 5,827,741 A | 10/1998 | Beattie et al. | |
| 5,837,736 A | 11/1998 | Mitchell et al. | |
| 5,840,759 A | 11/1998 | Mitchell et al. | |
| 5,910,316 A | 6/1999 | Keefer et al. | |
| 5,958,427 A | 9/1999 | Salzman et al. | |
| 5,962,520 A | 10/1999 | Smith et al. | |
| 6,110,453 A | 8/2000 | Keefer et al. | |
| 6,147,068 A | 11/2000 | Smith et al. | |
| 6,200,558 B1 | 3/2001 | Saavedra et al. | |
| 6,218,016 B1 | 4/2001 | Tedeschi et al. | |
| 6,232,336 B1 | 5/2001 | Hrabie et al. | |
| 6,232,434 B1 | 5/2001 | Stamler et al. | |
| 6,261,594 B1 | 7/2001 | Smith et al. | |
| 6,270,779 B1 | 8/2001 | Fitzhugh et al. | |
| 6,290,981 B1 | 9/2001 | Keefer et al. | |
| 6,359,182 B1 | 3/2002 | Stamler et al. | |
| 6,379,660 B1 | 4/2002 | Saavedra et al. | |
| 6,410,622 B1 | 6/2002 | Endres | |
| 6,451,337 B1 | 9/2002 | Smith et al. | |
| 6,511,991 B2 | 1/2003 | Hrabie et al. | |
| 6,576,258 B1 | 6/2003 | Kofler et al. | |
| 6,610,660 B1 | 8/2003 | Saavedra et al. | |
| 6,673,338 B1 * | 1/2004 | Arnold et al. | 424/78.16 |
| 6,673,891 B2 | 1/2004 | Stamler et al. | |
| 6,703,046 B2 | 3/2004 | Fitzhugh et al. | |
| 6,706,274 B2 | 3/2004 | Herrmann et al. | |
| 6,737,447 B1 | 5/2004 | Smith et al. | |
| 6,750,254 B2 | 6/2004 | Hrabie et al. | |
| 6,855,366 B2 | 2/2005 | Smith et al. | |
| 6,911,433 B2 | 6/2005 | Saavedra et al. | |
| 6,911,478 B2 | 6/2005 | Hrabie et al. | |
| 6,949,530 B2 | 9/2005 | Hrabie et al. | |
| 6,951,902 B2 | 10/2005 | McDonald et al. | |
| 7,105,502 B2 | 9/2006 | Arnold et al. | |
| 7,122,529 B2 | 10/2006 | Ruane et al. | |
| 7,135,189 B2 | 11/2006 | Knapp | |
| 7,169,404 B2 | 1/2007 | Hossainy et al. | |
| 2003/0077243 A1 * | 4/2003 | Fitzhugh et al. | 424/78.27 |
| 2003/0083739 A1 | 5/2003 | Cafferata | |
| 2003/0147845 A1 | 8/2003 | Saavedra et al. | |
| 2005/0203069 A1 | 9/2005 | Arnold et al. | |
| 2006/0008529 A1 | 1/2006 | Meyerhoff et al. | |

FOREIGN PATENT DOCUMENTS

| | | |
|---|---|---|
| WO | WO 95/24908 | 9/1995 |
| WO | WO 96/15781 | 5/1996 |
| WO | WO 96/15797 | 5/1996 |
| WO | WO 96/32136 | 10/1996 |
| WO | WO 98/19996 | 5/1998 |
| WO | WO 99/01427 | 1/1999 |
| WO | WO 99/33823 | 7/1999 |
| WO | WO 01/26702 A2 | 4/2001 |
| WO | WO 01/85227 A2 | 11/2001 |
| WO | WO 02/41902 A1 | 5/2002 |
| WO | WO 2005/039664 A2 | 5/2005 |
| WO | WO 2005/081752 A2 | 9/2005 |
| WO | WO 2005/081753 A3 | 9/2005 |
| WO | WO 2006/037105 A2 | 4/2006 |
| WO | WO 2006/064056 A2 | 6/2006 |
| WO | WO 2006/084909 A1 | 8/2006 |
| WO | WO 2006/084910 A2 | 8/2006 |
| WO | WO 2006/084911 A2 | 8/2006 |
| WO | WO 2006/084912 A1 | 8/2006 |
| WO | WO 2006/084913 A2 | 8/2006 |
| WO | WO 2006/100154 A1 | 9/2006 |
| WO | WO 2006/125016 A1 | 11/2006 |
| WO | WO 2006/128121 A2 | 11/2006 |
| WO | WO 2007/067477 A1 | 6/2007 |

OTHER PUBLICATIONS

Al-Sa'Doni et al., "Neocuproine, a Selective Cu(I) Chelator, and the Relaxation of Rat Vascular Smooth Muscle by S-nitrosothiols," *British J. of Pharm.*, 1997, vol. 121, pp. 1047-1050, Stockton Press.

Anastasiou et al., "Aminosalicylate-Based Biodegradable Polymers: Syntheses and in vitro Characterization of Poly(anhydride-ester)s and Poly(anhydride-amide)s," *J. of Polymer Science*: Part A: Polymer Chemistry, 2003, vol. 41, pp. 3667-3679, Wiley Periodicals, Inc.

Annich et al., "Reduced Platelet Activation and Thrombosis in Extracorporeal Circuits Coated with Nitric Oxide Release Polymers," *Crit. Care Med.*, 2000, vol. 28, No. 4, pp. 915-920.

Arnold et al., Mechanistic Insight into Exclusive Nitric Oxide Recovery from a Carbon-bound Diazeniumdiolate, *Nitric Oxide*, 2002, vol. 7, pp. 103-108, Academic Press.

Arnold et al., "A Nitric Oxide-Releasing Polydiazeniumdiolate Derived from Acetronitrile," *Org. Lett.*, 2002, vol. 4, No. 8, pp. 1323-1325, American Chemical Society.

Arnold et al., "Reaction of Nitric Oxide with Benzyl Cyanide to Yield a Bis-diazeniumdiolated Imidate," *Tetrahedron Lett.*, 2000, vol. 41, pp. 8421-8424, Elsevier Science Ltd.

Arnold et al., "Surprising Reactivity of C-based Diazeniumdiolats: Conversion of a Nitrile to an Imidate and its Decomposition to Yield Nitric Oxide," (#111.) *Abstracts of Papers*, Part 1, 220th ACS National Meeting, Aug. 20-24, 2000, Washington, D.C., American Chemical Socity.

Arulsamy et al., "Dipotassium Ethane-1,1-diylbis(diazeniumdiolate) Monohydrate," *Acta Cryst.*, 2005, Section E61, pp. m764-m766.

Arulsamy et al., "Disodium 3-oxobutane-2,2-diylbis-(diazeniumdiolate) Dihydrate," *Acta Cryst.*, 2005, Section E61, pp. m838-m840.

Arulsamy et al., "Disodium 4-hydroxybutane-1,1-diylbis-(diazeniumdiolate) Sesquihydrate," *Acta Cryst.*, 2005, Section E61, pp. m961-m963.

Arulsamy et al., "Multiplicity Control in the Polygeminal Diazeniumdiolation of Active Hydrogen Bearing Carbons: Chemistry of a New type of Trianionic Molecular Propeller," *J. Am. Chem. Soc.*, 2001, vol. 123, No. 44, pp. 10860-10869, American Chemical Society.

Arulsamy et al., "New Methanetrisdiazeniumdiolates," *Tetrahedron Lett.*, 2003, vol. 44, pp. 4267-4269, Elsevier Science Ltd.

Arulsamy et al., "Synthesis of Diazeniumdiolates from the Reactions of Nitric Oxide with Enolates," *J. Org. Chem.*, 2006, vol. 71, No. 2, pp. 572-581, American Chemical Society.

(56) References Cited

OTHER PUBLICATIONS

Arulsamy et al., "Traube's 'Oxazomalonic Acid' is a 3-Hydroxysydnone Carboxylate with an E-ONNO Geometry," *Angew. Chem. Int. Ed.*, 2002, vol. 41, No. 12, pp. 2089-2091, Germany.
Arulsamy et al., "Tripotassium Carboxylatomethylenebis(diazenium-diolate) 2.5-Hydrate," *Acta Cryst.*, 2005, Section E61, pp. m930-m932.
Askew et al., "Chemical Mechanisms Underlying the Vasodilator and Platelet Anti-Aggregating properties of S-Nitroso-N-acetyl-DL-penicillamine and S-Nitrosoglutathione," *Bioorganic & Medicinal Chem.*, 1995, vol. 3, No. 1, pp. 1-9, Elsevier Science Ltd., Great Britain.
Ausprunk et al., "Migration and Proliferation of Endothelial Cells in Preformed and Newly Formed Blood Vessels During Tumor Angiogenesis," *Microvascular Research*, 1977, vol. 14, pp. 53-65, Academic Press Inc., Great Britain.
Barrett al., "Role of Calcium in Angiotensin II-Mediated Aldosterone Secretion," *Endocrine Reviews*, Nov. 1989, vol. 10, No. 4, pp. 496-518, The Endrocrine Society, U.S.A.
Bhat et al., "N-Nitroso-N, O-dialkylhydroxylamines: preparation, structure, reaction," *J. Chem. Soc.*, Perkin Trans. 2, 2000, pp. 1435-1446, The Royal Society of Chemistry.
Bierbaum et al., "Growth of Self-Assembled n-Alkyltrichlorosilane Films on Si(100) Investigated by Atomic Force Microscopy," *Langmuir*, 1995, vol. 11, No. 6, pp. 2143-2150, American Chemical Society.
Bohle et al., "Cyclohexadienone Diazeniumdiolates from Nitric Oxide Addition," *J. Org. Chem.*, 2000, vol. 65, No. 18, pp. 5685-5692, American Chemical Society.
Bonifant et al., "Design and Synthesis of Arylated Diazeniumdiolates with Anti-leukemic Activity," (#292.), *Abstracts of Papers*, Part 2, 221$^{st}$ ACS National Meeting, Apr. 1-5, 2001, San Diego, CA, American Chemical Society.
Carre et al., "Convenient Preparation of Functionalised Polymer-Based Resins via an Economical Preparation of Chloromethylated Polystyrene Resins (Merrifield Type)," *Org. Process Research & Development*, 2000, vol. 4, No. 6, pp. 606-610, American Chemical Society and the Royal Society of Chemistry.
Charville et al., "Reduced *Escherichia coli* and *Staphylococcus Aureus* Adhesion via Xerogel-derived Nitric Oxide Release," PMSE 410, *Joint PMSE/POLY Poster Session*, The 232nd ACS National Meeting, Sep. 10-14, 2006, San Francisco, CA, (file://D:\232ND\PMSE\P1005084.HTM).
Chernoff et al., "The Cellular and Molecular Basis of the Platelet Storage Lesion: a Symposium Summary," *Transfusion*, 1992, vol. 32, No. 4, pp. 386-390.
Davies et al., "Diazeniumdiolate Prodrug Activation in Model Membrane Systems," INOR 138, , The 232nd ACS National Meeting, Sep. 10-14, 2006, San Francisco, CA, (file://D:\232ND\INOR\P9/4797.HTM).
De Groote et al., "NO Inhibitions: Antimicrobial Properties of Nitric Oxide," *CID*, 1995, vol. 21 (Suppl 2), pp. S162-S165.
DeRosa et al., "Nitric Oxide-Releasing Polymeric Materials Derived in Part From Acrylonitrile Monomer," (#247.) *Abstracts of Papers*, Part 2, 229$^{th}$ ACS National Meeting, Mar. 13-17, 2005, San Diego, CA, American Chemical Society.
Dicks et al., "Generation of Nitric Oxide from S-nitrosothiols using Protein-bound $Cu^{2+}$ Sources," *Chemistry & Biology*, 1996, vol. 3, No. 8, pp. 655-659.
Dobmeier et al., "Nitric Oxide-Releasing Xerogel-Based Fiber-Optic pH Sensors," *Anal. Chem.*, Nov. 1, 2006, vol. 78, No. 21, pp. 7461-7466.
Endo K., "Chemical Modification of Metallic Implant Surfaces with Biofunctional Proteins (Part 1) Molecular Structure and Biological Activity of a Modified NiTi Alloy Surface," *Dental Materials J.*, 1995, vol. 14, No. 2, pp. 185-198, Chemicon International Inc., Temecula (CA), Japan.

Espey et al., "A Chemical Perspective on the Interplay Between NO, Reactive Oxygen Species, and Reactive Nitrogen Oxide Species," *Ann. N.Y. Acad. Sci.*, 2002, vol. 962, pp. 195-206, New York Academy of Sciences.
Ferdinandy et al., "Nitric Oxide, Superoxide, and Peroxynitrite in Myocardial Ischaemia-Reperfusion Injury and Preconditioning," *British J. of Pharm.*, 2003, vol. 138, No. 4, pp. 532-543, Nature Publishing Group.
Fleser et al., "Nitric Oxide-Releasing Biopolymers Inhibit Thrombus Formation in a Sheep Model of Arteriovenous Bridge Grafts," *J. of Vascular Surgery*, Oct. 2004, vol. 40, No. 4, pp. 803-811, The Society for Vascular Surgery.
Freedman et al., "Glutathione Peroxidase Potentiates the Inhibition of Platelet Function by S-Nitrosothiols," *J. Clin. Invest.*, Jul. 1995, vol. 96, pp. 394-400, The American Society for Clinical Investigation, Inc.
Gordge et al., "Role of a Copper (I)-Dependent Enzyme in the Antiplatelet Action of S-nitrosoglutathione," *British J. of Pharm.*, 1996, vol. 119, pp. 533-538, Stockton Press.
Homer et al., "Cyclic GMP-Independent Relaxation of Rat Pulmonary Artery by Spermine NONOate, a Diazeniumdiolate Nitric Oxide Donor," *British J. of Pharm.*, 2000, vol. 131, pp. 673-682, Macmillan Publishers Ltd.
Hrabie et al., "Carbon-Bound Diazeniumdiolates from the Reaction of Nitric Oxide with Amidines," *J. Org. Chem.*, 2005, vol. 70, No. 19, pp. 7647-7653, American Chemical Society.
Hrabie et al., "Chemistry of the Nitric Oxide-Releasing Diazeniumdiolate ("Nitrosohydroxylamine") Functional Group and Its Oxygen-Substituted Derivatives," *Chem. Rev.*, 2002, vol. 102, No. 4, pp. 1135-1154, American Chemical Society.
Hrabie et al., "Conversion of Proteins to Diazeniumdiolate-Based Nitric Oxide Donors," *Bioconjugate Chem.*, 1999, vol. 10, No. 5, pp. 838-842, American Chemical Society.
Hrabie et al., "New Nitric Oxide-Releasing Zwitterions Derived from Polyamines," *J. Org. Chem.*, 1993, vol. 58, No. 6, pp. 1472-1476, American Chemical Society.
Hrabie et al., "Reaction of Nitric Oxide at the β-Carbon of Enamines. A New Method of Preparing Compounds Containing the Diazeniumdiolate Functional Group," *J. Org. Chem.*, 2000, vol. 65, No. 18, pp. 5745-5751, American Chemical Society.
Jourd'Heuil et al., "Effect of Superoxide Dismutase on the Stability of S-Nitrosothiols," *Archives of Biochemistry and Biophysics*, Jan. 15, 1999, vol. 361, No. 2, pp. 323-330, Academic Press.
Jourd'Heuil et al., "Nitric Oxide and the Gut," (Small Intestine), *Current Gastroenterology Reports*, 1999, vol. 1, pp. 384-388, Current Science Inc. (ISSN 1522-8037).
Jun et al., "Nitric Oxide-Producing Polyurethanes," *Biomacromolecules*, 2005, vol. 6, No. 2, pp. 838-844, American Chemical Society.
Kader et al., "eNOS-Overexpressing Endothelial Cells Inhibit Platelet Aggregation and Smooth Muscle Cell Proliferation in Vitro," *Tissue Engineering*, 2000, vol. 6, No. 3, p. 241-251, Mary Ann Liebert, Inc.
Kano et al., "N-Nitrosohydroxylamines. 2. Thermal Decomposition of N,O-Dibenzyl-N-nitrosohydroxylamines," *J. Org. Chem.*, 1993, vol. 58, No. 6, pp. 1564-1567, American Chemical Society.
Katritzky et al., "Utilization of Pyridinium Salts as Microsensor Coatings," *Langmuir*, 1989, vol. 5, pp. 1087-1092, American Chemical Society.
Kaul et al., "Polymeric-Based Perivascular Delivery of a Nitric Oxide Donor Inhibits Intimal Thickening After Balloon Denudation Arterial Injury: Role of Nuclear Factor-kappaB," *JACC*, Feb. 2000, vol. 35, No. 2, pp. 493-501, Elsevier Science Inc.
Keefer et al., "Chemistry of the Diazeniumdiolates," *Nitric Oxide: Biology and Chemistry*, 2001, vol. 5, No. 4, pp. 377-394.
Keefer L., "Nitric Oxide (NO)- and Nitroxyl (HNO)-Generating Diazeniumdiolates (NONOates): Emerging Commercial Opportunities," *Current Topics in Medicinal Chemistry*, 2005, vol. 5, No. 7, pp. 625-636, Bentham Science Publishers Ltd.
Keefer L., "Progress Toward Clinical Application of the Nitric Oxide-Releasing Diazeniumdiolates," *Annu. Rev. Pharmacol. Toxicol.*, 2003, (plus figures and table of contents), vol. 43, pp. 585-607.

(56) References Cited

OTHER PUBLICATIONS

Kern et al., "Durability of Resin Bonds to Pure Titanium," *J. of Prosthodontics*, Mar. 1995, vol. 4, No. 1, pp. 16-22, American College of Prosthodontists.

Klinger M., "The Storage Lesion of Platelets: Ultrastructural and Functional Aspects," *Ann. Hematol.*, 1996, vol. 73, pp. 103-112, Springer-Verlag.

Kowaluk et al., "Metabolic Activation of Sodium Nitroprusside to Nitric Oxide in Vascular Smooth Muscle," *J. of Pharmacology and Experimental Therapeutics*, 1992, vol. 262, No. 3, pp. 916-922, American Society for Pharmacology and Experimental Therapeutics, U.S.A.

LeRoy et al., "A Method for Studying Small Intestinal Transit in the Rat," *Anals N.Y. Academy of Sciences*, Fourth Colloquium in Biological Sciences: Blood-Brain Transfer, Jun. 14, 1988, vol. 529, pp. 131-134.

Liu et al., "S-Transnitrosation Reactions are Involved in the Metabolic Fate and Biological Actions of Nitric Oxide," *J. of Pharmacology and Experimental Therapeutics*, 1998, vol. 284, No. 2, pp. 526-534, American Society for Pharmacology and Experimental Therapeutics, U.S.A.

Lopez et al., "Novel Diazeniumdiolates Nitric Oxide Donors for Biomedical Applications," (#297.), *Abstracts of Papers*, Part 2, 224$^{th}$ ACS National Meeting, Aug. 18-22, 2002, Boston, MA, American Chemical Society.

Marletta et al., "Unraveling the Biological Significance of Nitric Oxide," *BioFactors*, 1990, vol. 2, No. 4, pp. 219-225, Oxford University Press.

Marxer et al., "Nitric Oxide Releasing Sol-Gel Materials: Towared Improved Subcutaneous Sensors," (#104.), *Abstracts of Papers*, 222$^{nd}$ ACS National Meeting, Aug. 26-30, 2001, Chicago, IL, American Chemical Society.

Marxer et al., "Preparation of Nitric Oxide (NO)-Releasing Sol-Gels for Biomaterial Applications," *Chem. Mater.*, 2003, vol. 15, No. 22, pp. 4193-4199, American Chemical Society.

Marxer et al., "Sol-Gel Derived Nitric Oxide-Releasing Oxygen Sensors," *The Analyst*, 2005, vol. 130, pp. 206-212, The Royal Society of Chemistry.

McLaughlin-Borlace et al., "Bacterial Biofilm on Contact Lenses and Lens Storage Cases in Wearers with Microbial Keratitis," *J. of Applied Microbiology*, 1998, vol. 84, pp. 827-838, The Society for Applied Microbiology.

Merrifield R., "Solid Phase Peptide Synthesis. I. The Synthesis of a Tetrapeptide," *Synthesis of a Tetrapeptide*, Jul. 20, 1963, vol. 85, pp. 2149-2154.

Meyer et al., "Kinetics and Equilibria of S-nitrosothiol-thiol Exchange Between Glutathione, Cysteine, Penicillamines and Serum Albumin," *FEBS Letters*, 1994, vol. 345, pp. 177-180, Federation of European Biochemical Societies.

Meyerhoff et al., "Enhancing the Biocompatibility and In Vivo Performance of Intravascular Chemical Sensors Using Nitric Oxide Release Polymers," (#132.), *Abstracts of Papers*, Part 1, 218$^{th}$ ACS National Meeting, Aug. 22-26, 1999, New Orleans, LA, American Chemical Society.

Mohanraj et al., "Phase-Transfer-Catalyzed Chlorination of Poly(p-methylstyrene)," *Macromolecules*, 1986, vol. 19, pp. 2470-2472, American Chemical Society.

Moncada et al., "Relationship Between Prostacyclin and Nitric Oxide in the Thrombotic Process," *Thrombosis Research Supplement XI*, 1990, pp. 3-13, Pergamon Press plc.

Moncada et al., "Nitric Oxide: Physiology, Pathophysiology, and Pharmacology," *Pharmacological Reviews*, 1991, vol. 43, No. 2, pp. 109-142, The American Society for Pharmacology and Experimental therapeutics.

Mooradian et al., "Nitric Oxide (NO) Donor Molecules: Effect of NO Release Rate on Vascular Smooth Muscle Cell Proliferation In Vitro," *J. Cardiovasc. Pharmacol.*, 1995, vol. 25, No. 4, pp. 674-678, Raven Press, Ltd., NY.

Morley et al., "Mechanism of Vascular Relaxation Induced by the Nitric Oxide (NO)/Nucleophile Complexes, a New Class of NO-Based Vasocilators," *J. Cardiovasc. Pharmacol.*, 1993, vol. 21, No. 4, pp. 670-676, Raven Press, Ltd, NY.

Mowery et al., "Preparation and Characterization of Hydrophobic Polymeric Films that are Thromboresistant Via Nitric Oxide Release," *Biomaterials*, 2000, vol. 21, pp. 9-21, Elsevier Science Ltd.

Mowery et al., "More Biocompatible Electrochemical Sensors Through the Use of Combined Nitric Oxide Release/Ion Sensing Polymeric Films," (#339.), *Abstracts of Papers*, Part 2, 213$^{th}$ ACS National Meeting, Apr. 13-17, 1997, San Francisco, CA, American Chemical Society.

Mowery et al., "Polymeric Diazeniumdiolates for Fabricating Thromboresistant Electrochemical Sensors Via Nitric Oxide Release," (#034.), *Abstracts of Papers*, Part 2, 216$^{th}$ ACS National Meeting, Aug. 23-27, 1998, Boston, MA, American Chemical Society.

Nablo et al., "In Vitro Cytotoxicity of Nitric Oxide-Releasing Sol-Gel Derived Materials," *Biomaterials*, 2005, vol. 26, pp. 4405-4415, Elsevier Ltd.

Nablo et al., "Nitric Oxide-Releasing Sol-Gels as Antibacterial Coatings for Orthopedic Implants," *Biomaterials*, 2005, vol. 26, pp. 917-924, Elsevier Ltd.

Nablo et al., "Sol-Gel Derived Nitric-Oxide Releasing Materials that Reduce Bacterial Adhesion," *J. Am. Chem. Soc.*, 2001, vol. 123, No. 39, pp. 9712-9713, American Chemical Society.

Neergaard L., "FDA Approves Stent that Emits Medication" *Milwaukee Journal Sentinel*, Apr. 2003, 2 pages [retrieved online on Jun. 17, 2007]. Retrieved from the Internet: <URL: http://findarticles.com/p/articles/mi_qn4196/is_20030425/ai_n10868900/print>.

Oliver et al., "The Internal Calcium Concentration of Human Platelets Increases During Chilling," *Biochimica et Biophysica Acta*, 1999, vol. 1416, pp. 349-360, Elsevier Science B.V.

Palmer et al., "A Novel Citrulline-Forming Enzyme Implicated in the Formation of Nitric Oxide by Vascular Endothelial Cells," *Biochemical and Biophysical Research Communications*, Jan. 16, 1989, vol. 158, No. 1, pp. 348-352, Academic Press, Inc.

Parzuchowski et al., "Synthesis and Characterization of Polymethacrylate-Based Nitric Oxide Donors," *J. Am. Chem. Soc.*, 2002, vol. 124, No. 41, pp. 12182-12191, American Chemical Society.

Passerini, D., "The Design, Synthesis, and Characterization of Lung Specific Polyamine Diazeniumdiolates in the Treatment of Pulmonary Hypertension," *Dissertation Abstracts International*, Jan. 2000, vol. 60, No. 7, pp. 3269-B (ISSN 0419-4217) (Order No. DA 9940593).

Rao et al., "Poly(butanediol Spermate): A Hydrolytically Labile Polyester-Based Nitric Oxide Carrier," *J. Bioactive and Compatible Polymers*, Jan. 1999, vol. 14, No. 1, pp. 54-63, Technomic Publishing Co. Inc.

Raulli R., "Inhibition of Human Platelet Aggregation by Diazeniumdiolates: Extent of Inhibition Correlates with Nitric Oxide Load Delivered," *J. Pharm. Pharmacol.*, 1998, vol. 50, pp. 75-82.

Reynolds et al., "Bis-diazeniumdiolates of Dialkyldiamines: Enhanced Nitric Oxide Loading of Parent Diamines," *Org. Lett.*, 2005, vol. 7, No. 14, pp. 2813-2816, American Chemical Society.

Reynolds et al., "Nitric Oxide Releasing Polyurethanes with Covalently Linked Diazeniumdiolated Secondary Amines," *Biomacromolecules*, 2006, vol. 7, No. 3, pp. 987-994, American Chemical Society.

Saavedra et al., "Chemistry of the Diazeniumdiolates. O- versus N-Alkylation of the RNH[N(O)NO] Ion," *J. Am. Chem. Soc.*, 2004, vol. 126, No. 40, pp. 12880-12887, American Chemical Society.

Saavedra et al., "Conversion of a Polysaccharide to Nitric Oxide-Releasing Form. Dual-Mechanism Anticoagulant Activity of Diazeniumdiolated Heparin," *Bioorg. Med. Chem. Lett.*, 2000, vol. 10, pp. 751-753, Elsevier Science Ltd.

Saavedra J., "Nitrogen-Based Diazeniumdiolates: Versatile Nitric Oxide-Releasing Compounds in Biomedical Research and Potential Clinical Applications," *J. Chem. Ed.*, Dec. 2002, vol. 79, No. 12, pp. 1427-1434.

Saavedra et al., "Synthesis of Labile Diazeniumdiolate Prodrugs for Controlled Delivery of Nitric Oxide," (#113.), *Book of Abstracts*, ACS National Meeting, Mar. 26-30, 2000, San Francisco.

(56) References Cited

OTHER PUBLICATIONS

Sagiv J., "Organized Monolayers by Adsorption. I. Formation and Structure of Oleophobic Mixed Monolayers on Solid Surfaces," *J. Am. Chem. Soc.*, Jan. 2, 1980, vol. 102, No. 1. pp. 92-98, American Chemical Society.

Schmeltzer et al., "Optimized Synthesis of Salicylate-based Poly(anhydride-esters)," *Polymer Bulletin*, 2003, vol. 49, pp. 441-448, Springer-Verlag.

Schmidt et al., "Determination of Nitrite and Nitrate by the Griess Reaction," *Methods in Nitric Oxide Research*, 1996, pp. 491-497, John Wiley & Sons.

Schwartz et al., "Drug-Eluting Stents in Preclinical Studies: Recommended Evaluation From a Consensus Group," *Circulation* (Journal of the American Heart Association), Oct. 1, 2002, pp. 1866-1873.

Sekhar et al., "Dimethyl Suberimidate as an Effective Crosslinker for Antibody-Enzyme Conjugation," *Preparative Biochemistry*, 1991, vol. 21, No. 4, pp. 215-227, Marcel Dekker, Inc.

Serhatkulu S., "Diazeniumdiolates of Chitosan Derivatives and Polyethyleneimine for Controlled Selective Delivery of Nitric Oxide," *Dissertation Abstracts International*, May 2000, vol. 60, No. 11, p. 5503-B (ISSN 0419-4217) (Order No. DA9951317).

Shami et al., "Antitumor Activity of JS-K [$O^2$-(2,4-Dinitrophenyl) 1-[(4-Ethoxycarbonyl)piperazin-1-yl]diazen-1-ium-1,2-diolate] and Related $O^2$-Aryl Diazeniumdiolates in Vitro and in Vivo," *J. Med. Chem.*, 2006, vol. 49, No. 14, pp. 4356-4366, American Chemical Society.

Sheng et al., "Selective Functionalization of Poly(4-methylstyrene)," *Macromolecules*, 1997, vol. 30, No. 21, pp. 6451-6457, American Chemical Society.

Showalter et al., "Potential Prodrugs of Nitric Oxide-Releasing Proli/NO," (#237.), *Abstracts of Papers*, Part 2, 227th ACS National Meeting, Mar. 28-Apr. 1, 2004, Anaheim, CA, American Chemical Society.

Showalter et al., "Synthesis and Chemistry of Diazeniumdiolate Anions from Hindered Amines," *Abstracts of Papers*, Part 2, 225th ACS National Meeting, Mar. 23-27, 2003, New Orleans, LA, American Chemical Society.

Silberzan et al., "Silanation of Silica Surfaces. A New Method of Constructing Pure or Mixed Monolayers," *Langmuir*, 1991, vol. 7, No. 8, pp. 1647-1651, American Chemical Society.

Sim et al., "Solid-Phase C-Acylation of Active Methylene Compounds," *Tetrahedron Lett.*, 1998, vol. 39, pp. 2195-2198, Elsevier Science Ltd.

Simmons M., "Transdermal Delivery of Nitric Oxide Via Diazeniumdiolates with Optimization and Penetration Enhancement Methods," *Dissertation Abstracts International*, Jul. 1998, and vol. 59, No. 1, p. 180-B (ISSN 0419-4217) (Order No. DA9821359).

Smith et al., "Transdermal Delivery of Nitric Oxide from Diazeniumdiolates," *J. Controlled Release*, 1998, vol. 51, pp. 153-159, Elsevier Science B.V.

Snyder E., "Activation During Preparation and Storage of Platelet Concentrates," *Transfusion*, 1992, vol. 32, No. 6, pp. 500-502.

Srinivasan et al., "Alkyltrichlorosilane-Based Self-Assembled Monolayer Films for Stiction Reduction in Silicon Micromachines," *J. Microelectromechanical Systems*, Jun. 1998, vol. 7, No. 2, pp. 252-260, a Joint IEEE/ASME Publication.

Stasko et al., "Dendrimers as a Scaffold for Nitric Oxide Release," *J. Am. Chem. Soc.*, 2006, vol. 128, No. 25, pp. 8265-8271, American Chemical Society.

Tierney et al., "Prevention and Reversal of Experimental Posthemorrhagic Vasospasm by the Periadventitial Administration of Nitric Oxide from a Controlled-release Polymer," *Neurosurgery*, Oct. 2001, vol. 49, No. 4, pp. 945-953.

Tillman et al., "Formation of Multilayers by Self-Assembly," *Langmuir*, 1989, vol. 5, pp. 101-111, American Chemical Society.

Traube von W., "Ueber Synthesen Stickstoffhaltiger Verbindungen mit Hülfe des Stickoxyds," pp. 81-128, 2010.

Trujillo et al., "Xanthine Oxidase-mediated Decomposition of S-Nitrosothiols," *J. Biological Chemistry*, Apr. 3, 1998, vol. 273, No. 14, pp. 7828-7834, The American Society for Biochemistry and Molecular Biology, Inc.

Tutusaus et al., "Kharasch Addition Catalysed by Half-Sandwich Ruthenium Complexes. Enhanced Activity of Ruthenacarboranes," *Tetrahedron Lett.*, 2003, vol. 44, pp. 8421-8425, Elsevier Ltd.

Ulman A., "Formation and Structure of Self-Assembled Monolayers," *Chem. Rev.*, 1996, vol. 96, No. 4, pp. 1533-1554, American Chemical Society.

Verma et al., "Nitric Oxide-Eluting Polyurethanes—Vascular Grafts of the Future?," *N. Engl. J. Med.*, Aug. 18, 2005, vol. 353, No. 7, pp. 730-731, Massachusetts Medical Society.

Wang et al., "Chemistry of the Diazeniumdiolates: Z ⇌ E Isomerism," *J. Am. Chem. Soc.*, 2005, vol. 127, No. 15, pp. 5388-5395, American Chemical Society.

Wasserman et al., "Structure and Reactivity of Alkylsiloxane Monolayers Formed by Reaction of Alkyltrichlorosilanes on Silicon Substrates," *Langmuir*, 1989, vol. 5, No. 4, pp. 1074-1087, American Chemical Society.

Wink et al., "Chemical Biology of Nitric Oxide: Regulation and Protective and Toxic Mechanisms," *Current Topics in Cellular Regulation*, 1996, vol. 34, pp. 159-187, Academic Press, Inc.

Wink et al., "Nitric Oxide Protects Against Cellular Damage and Cytotoxicity from Reactive Oxygen Species," *Proc. Natl. Acad. Sci. USA*, Nov. 1993, vol. 90, pp. 9813-9817.

Winkler T., "Synthese und Untersuchung der NO-Freisetzungskinetik in wässrigen Medien und unter dem Einfluss von Cytochrom P-450-imitierenden biomimetischen Systemen" (Dissertation), 2006, Hamburg, pp. 1-221.

Winokur et al., "Mechanism of Shape Change in Chilled Human Platelets," *Blood*, Apr. 1, 1995, vol. 85, No. 7, pp. 1796-1804, The American Society of Hematology.

Wolkers et al., "From Anhydrobiosis to Freeze-drying of Eukaryotic Cells," *Comparative Biochemistry and Physiology*, Part A, 2002, vol. 131, pp. 535-543, Elsevier Science Inc.

Yang et al., "Microstamping of a Biological Ligand Onto an Activated Polymer Surface," *Adv. Mater.*, 2000, vol. 12, No. 6, pp. 413-417, Wiley-Vch Verlag GmbH.

Yoshida et al., "Thin Sol-Gel-Derived Silica Coatings on Dental Pure Titanium Casting", Department of Fixed Prosthodontics, Nagasaki University School of Dentistry, Nagasaki, Japan and Materials Section, Technology Center of Nagasaki, Omura, Japan, 1999, pp. 778-785, John Wiley & Sons, Inc. (CCC 0021-9304/99/060778-08).

Zai et al., "Cell-Surface Protein Disulfide Isomerase Catalyzes Transnitrosation and Regulates Intracellular Transfer of Nitric Oxide," *J. Clinical Investigation*, Feb. 1999, vol. 103, No. 3, pp. 393-399.

Zhang et al., "Nitric Oxide-Releasing Fumed Silica Particles: Synthesis, Characterization, and Biomedical Application," *J. Am. Chem. Soc.*, 2003, vol. 125, No. 17, pp. 5015-5024, American Chemical Society.

Zhang et al., "Nitric Oxide Releasing Silicone Rubbers with Improved Blood Compatibility: Preparation, Characterization, and In Vivo Evaluation," *Biomaterials*, 2002, vol. 23, pp. 1485-1494, Elsevier Science Ltd.

Zhang et al., "Novel Silicone Materials with Improved Thromboresistance Via Nitric Oxide Release," (#251.), *Abstracts of Papers*, Part 2, 221st ACS National Meeting, Apr. 1-5, 2001, San Diego, CA, American Chemical Society.

Zhang et al., "Polymer Films or Coatings Embedded with Nitric Oxide Releasing Fumed Silica Particles," (#8.), *Abstracts of Papers*, Part 2, 222nd ACS National Meeting, Aug. 26-30, 2001, Chicago, IL, American Chemical Society.

Zhang et al., "Potentially More Blood Compatible Polymers Using Nitric Oxide Release Fumed Silica Fillers," (#40.), *Abstracts of Papers*, Part 2, 220th ACS National Meeting, Aug. 20-24, 2000, Washington, DC, American Chemical Society.

Zhou et al., "Polymethacrylate-Based Nitric Oxide Donors with Pendant N-Diazeniumdiolated Alkyldiamine Moieties: Synthesis, Characterization, and Preparation of Nitric Oxide Releasing Polymeric Coatings," *Biomacromolecules*, 2005, vol. 6, No. 2, pp. 780-789, American Chemical Society.

(56) References Cited

OTHER PUBLICATIONS

Zhou et al., "Preparation and Characterization of Polymeric Coatings with Combined Nitric Oxide Release and Immobilized Active Heparin," *Biomaterials*, 2005, vol. 26, pp. 6506-6517, Elsevier Ltd.
Office Action issued in the corresponding Canadian Patent Application No. 2,555,591, dated Feb. 2, 2010.
Office Action issued in the corresponding Indian Patent Application No. 4611/DELNP/2008.

Batchelor, et al., "More Lipophlic Dialkyldiamine-Based Diazeniumdiolates: Synthesis, Characterization, and Application in Preparing Thromboresistant Nitric Oxide Release Polymeric Coatings", *J. Med. Chem.*, vol. 46, No. 24, 2003, pp. 5153-5161.
Smith, et al., Nitric Oxide-Releasing Polymers Containing the [N(O)NO] Group, J. Med. Chem., vol. 39, No. 5, 1996, pp. 1148-1156.

* cited by examiner

NITRIC OXIDE-RELEASING POLYMERS

This application claims priority under 35 U.S.C. §120 to U.S. Provisional Application No. 60/542,277 filed Feb. 9, 2004, and to U.S. Provisional Application No. 60/542,298 filed Feb. 9, 2004, each of which is incorporated herein by reference in its entirety.

This work was sponsored by U.S. Public Health Service Grant No. R44 HL062729 from the National Heart Lung and Blood Institute of The National Institutes of Health.

BACKGROUND OF THE INVENTION

Field of the Invention

The present invention relates generally to nitric oxide-releasing polymers. More specifically, the present invention relates to carbon-based diazeniumdiolate nitric oxide-releasing polymers. The present invention also provides methods for a novel class of coatings in which NO-releasing carbon-based diazeniumdiolates may be covalently linked to a surface, whereby the release of NO imparts increased biocompatibility or other beneficial properties to the coated surface. One possible preferred application for this class of coatings would be in medical devices.

Nitric oxide (NO) is a bioregulatory molecule with diverse functional roles in cardiovascular homeostasis, neurotransmission and immune response (Moncada et al., 1990; Marletta et al., 1990). Because NO influences such a vast array of physiological activity, it is desirable to have compounds release NO for use as drugs and physiological and pharmacological research tools. Even more desirable are non-toxic, non-carcinogenic compounds that can generate NO under physiological conditions for therapeutic and clinical applications. Such compounds, however, have been difficult to develop.

Small molecules (generally described as molecules with Formula Weights less than 600) that release NO are well known, and some classes such as the organic nitrates have been used for decades therapeutically. These, however, are difficult to administer as they may circulate throughout the body causing a myriad of physiological effects leading to disturbances of homeostasis. For many therapeutic applications a more localized release of NO would be preferred.

More recently, polymeric forms of NO-releasing compounds have been described where the NO donor molecule is part of, associated with, incorporated in, or otherwise bound to a polymer matrix. The vast majority of polymeric NO donors are of the nitrogen- or N-based diazeniumdiolate class disclosed in U.S. Pat. No. 5,405,919, Keefer and Hrabie; U.S. Pat. No. 5,525,357, Keefer et al; U.S. Pat. No. 5,632,981, Saavedra et al.; U.S. Pat. No. 5,676,963 Keefer and Hrabie; U.S. Pat. No. 5,691,423, Smith et al.; U.S. Pat. No. 5,718,892 Keefer and Hrabie; U.S. Pat. No. 5,962,520, Smith and Rao; U.S. Pat. No. 6,200,558, Saavedra et al.; U.S. Pat. No. 6,270,779, Fitzhugh et al.; U.S. Patent Application Publication; Pub. No.: US 2003/0012816 A1, West and Masters. Diazeniumdiolates are a class of compounds which contain the —[N(O)NO]— functional group and have been known for over 100 years (Traube, 1898).

While N-based diazeniumdiolate polymers have the advantages of localized spontaneous and generally controllable release of NO under physiological conditions, a major disadvantage associated with all N-based diazeniumdiolates is their potential to form carcinogenic nitrosamines upon decomposition as shown in Equation 1 (Parzuchowski et al., 2002). Some nitrosamines are extremely carcinogenic and the potential for nitrosamine formation limits the N-based diazeniumdiolate class of NO donors from consideration as therapeutic agents based on safety issues.

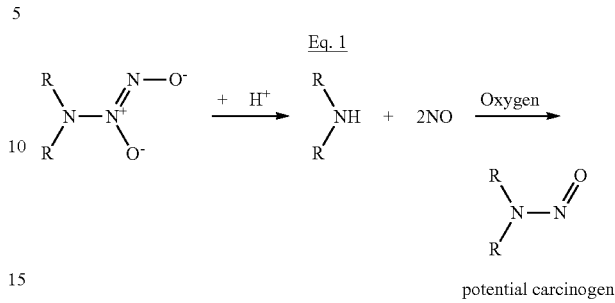

Eq. 1 potential carcinogen

Other non-diazeniumdiolate forms of polymeric NO donors have been described including S-nitroso compounds (U.S. Pat. Nos. 5,770,645 and 6,232,434, Stamler et al.) and C-nitroso compounds (U.S. Pat. No. 5,665,077, Rosen et al.; and U.S. Pat. No. 6,359,182, Stamler et al.). Regarding the S-nitroso compounds, their therapeutic potential is limited due to their rapid and unpredictable decomposition (release of NO) in the presence of trace levels of Cu(I) and possibly Cu(II) ions (Dicks et al., 1996; Al-Sa'doni et al., 1997). Furthermore, S-nitroso compounds may decompose by direct transfer of NO to reduced tissue thiols (Meyer et al., 1994; Liu et al., 1998). Finally, many mammalian enzymes may catalyze the release of NO from S-nitroso compounds (Jourd"heuil et al, 1999a; Jourd"heuil et al., 1999b; Askew et al., 1995; Gordge et al., 1996; Freedman et al., 1995; Zai et al., 1999; Trujillo et al., 1998). However tissue and blood levels of ions, enzymes, and thiols are subject to a wide range of variability in each individual, making the release of NO unpredictable from subject to subject. The dependence and sensitivity of NO release on blood and tissue components limits the therapeutic potential of nitroso compounds in medicine.

Several references to carbon- or C-based diazeniumdiolate small molecules (small molecules are generally described as molecules with a Formula Weight of 600 or less) which release NO have been disclosed (U.S. Pat. Nos. 6,232,336; 6,511,991; 6,673,338; Arnold et al. 2000; Arnold et al. 2002a; Arnold et al. 2002b). C-based diazeniumdiolates are desirable because in contrast to N-based diazeniumdiolates they are structurally unable to form nitrosamines while maintaining their ability spontaneously release NO under physiological conditions. Furthermore, there have been recently published reports on NO-releasing imidates, methanetrisdiazeniumdiolate, and a bisdiazeniumdiolate derived from 1,4-benzoquinone dioxime which released 2 moles of NO per mole of compound. (Arnold et al. 2000; Arnold et al. 2002a; Arnold et al. 2002b). While the NO-releasing properties of these small molecules are favorable, small molecules are very difficult to localize in the body after administration and tend to diffuse easily throughout the body, resulting in possible systemic side effects of NO. An additional problem specific to imidate- and thioimidate-derived molecules is that the protein binding properties of imidates may be undesirable in applications involving contact with blood, plasma, cells, or tissue because the imidate may react to form a covalent bond with tissue protein (see below).

Recently, carbon- or C-based diazeniumdiolate polymers have been disclosed (U.S. Pat. No. 6,673,338, Arnold et al., 2004). C-based diazeniumdiolates are desirable because in contrast to N-based diazeniumdiolate they are structurally unable to form nitrosamines while maintaining their ability spontaneously release NO under physiological conditions. Arnold et al. disclose imidates and thioimidates of the following general structure (1):

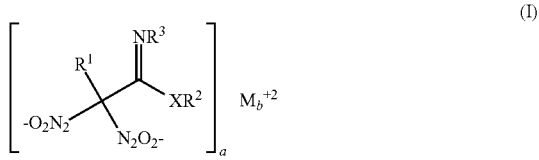

where $R^1$ is a polymer in one embodiment. They also disclose embodiments where the imidate functional group is used to bind the molecule to polymers or biopolymers (proteins), as the imidate functional group is commonly used to bind and/or cross-link proteins (Sekhar et al., 1991; Ahmadi and Speakman, 1978). However the protein binding properties of imidates would be undesirable in applications involving contact with blood, plasma, cells, or tissue because the imidate may react with protein tissue.

Thus there continues to be a need for NO-releasing polymers that release NO spontaneously under physiological conditions and in predictable and tunable quantities, where the NO release is not affected by metals, thiols, enzymes, or other tissue factors that may result in variable NO release, and where the polymer cannot decompose to form nitrosamines and does not covalently bind proteins.

Therefore, it is an object of the present invention to provide a composition that includes a C-based diazeniumdiolate covalently attached to a polymeric backbone that can generate localized fluxes of NO spontaneously under physiological conditions. It is a further object of the present invention to provide NO-releasing polymers that generate predictable and tunable NO release rates. It is a further object of the present invention to provide diazeniumdiolate polymers that do not decompose into nitrosamines or covalently bind proteins.

In addition, it is an object of the present invention to provide a method of synthesis for the polymer bound C-based diazeniumdiolates. A further object of the present invention is to provide methods of use for the C-based diazeniumdiolate polymers in biology and medicine. Further objects and advantages of the invention will become apparent from the following descriptions.

BRIEF SUMMARY OF THE INVENTION

The present invention accomplishes the above-described objects by providing a polymer composition that spontaneously releases NO under physiological conditions, without the possibility to form nitrosamines. The present invention provides a composition for the generation of NO from a C-based diazeniumdiolate that is covalently attached to a phenyl-containing polymer. The present inventors have developed an alternative means of introducing the —[N(O)NO]⁻ functional group into a polymeric backbone by attachment of the —[N(O)NO]⁻ group to the polymer via a carbon atom, with the general formula:

$$R^3\text{---}C(R^1)_x(N_2O_2R^2)_y \quad \text{FORMULA 1}$$

where y may be 1-3 and x may be 0-2 and the sum of x plus y equals 3, $R^1$ is not an imidate or thioimidate. $R^1$ may be represented by, but not limited to an electron withdrawing group such as, but not limited to, a cyano group; an ether group, such as, but not limited to —OCH$_3$, —OC$_2$H$_5$, and —OSi(CH$_3$)$_3$; a tertiary amine; or a thioether, such as, but not limited to, —SC$_2$H$_5$, and —SPh (substituted or unsubstituted). The $R^1$ group may also be a amine, such as, but not limited to, —N(C$_2$H$_5$)$_2$. $R^2$ is a countercation or organic group and $R^3$ is a phenyl group. The phenyl group may be pendant from the polymer backbone (as shown in Formula 2) or part of the polymer backbone (as shown in Formula 3). In addition to the aforementioned advantages of this technology over the prior art, manipulation of the $R^1$ group in Formula 1 can alter the release kinetics and the amount of NO released. Alterations of the $R^1$ group to alter the quantity and kinetics of NO-released are described below.

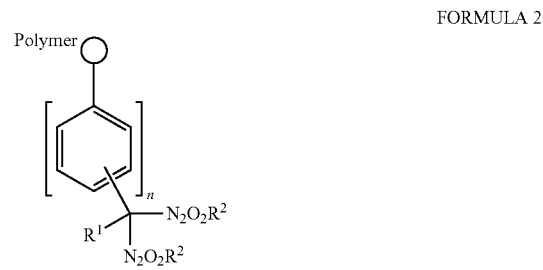

FORMULA 2

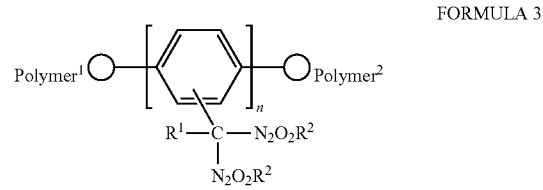

FORMULA 3

DETAILED DESCRIPTION OF THE INVENTION

Figure 1:
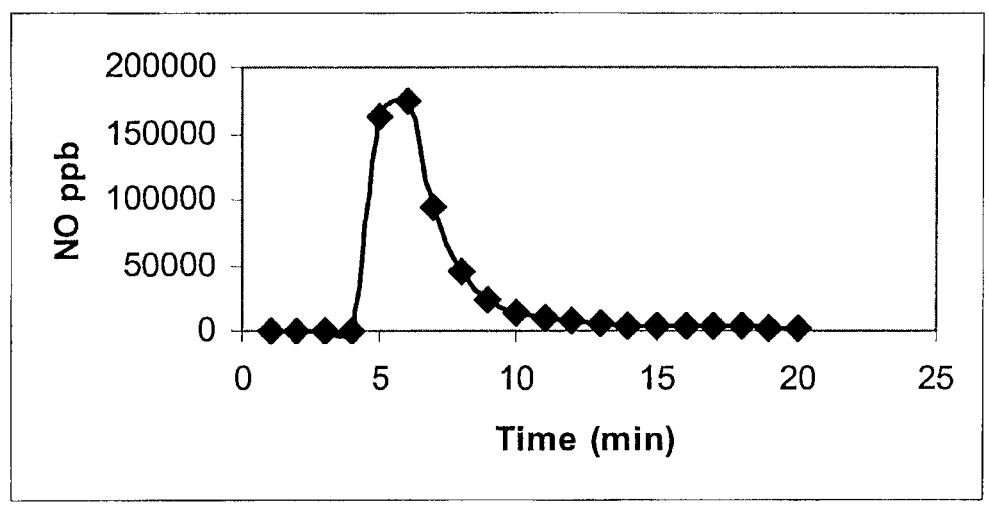
FIG. 1 shows the quantity of NO released from 5.5 mg of cyano-modified chloromethylated polystyrene diazeniumdiolate in pH 7.4 buffer over a 15 minute time period. Over this time period, 0.49 μmoles of NO per mg resin was produced. The quantity of NO released is measured in parts per billion (ppb), which is assessed and measured as described herein.

The present invention provides for a novel class of polymeric materials that contain the —[N(O)NO]⁻ functional group bound to a carbon atom. The C-based polymeric diazeniumdiolates of the present invention are useful for a number of reasons. For example, C-based polymeric diazeniumdiolates are advantageous as pharmacological agents, research tools, or as part of a medical device due to their ability to release pharmacologically relevant levels of nitric oxide under physiological conditions without the possibility of forming potent nitrosamine carcinogens. The C-based polymeric diazeniumdiolates of the present invention are insoluble. This property gives this class of materials a number of uses and advantages, including but not limited to: 1) delivery of NO to static or flowing aqueous solutions; and 2) the ability to remove the polymer from a solution or suspension by filtration or separation after it has delivered nitric oxide. Furthermore, the insoluble polymeric nature of the material allows embodiments of this invention to be used to construct NO-releasing medical devices.

In Formulas 1, 2, and 3, $R^1$ may not be represented by an imidate or thioimidate. $R^1$ may be represented by, but is not limited to an electron withdrawing group such as but not limited to a cyano group; an ether group, such as, but not limited to —$OCH_3$, —$OC_2H_5$, and —$OSi(CH_3)_3$; a tertiary amine; or a thioether, such as, but not limited to, —$SC_2H_5$, and —SPh (where the Ph is substituted or unsubstituted). The $R^1$ group may also be a amine, such as, but not limited to, —$N(C_2H_5)_2$, and in a preferred embodiment is an amine other than an enamine.

The $R^2$ group in Formulas 1, 2, and 3 may be a countercation or a covalently bound protecting group. In embodiments where the $R^2$ group is a countercation, the $R^2$ group may be any countercation, pharmaceutically acceptable or not, including but not limited to alkali metals such as sodium, potassium, lithium; Group IIa metals such as calcium and magnesium; transition metals such as iron, copper, and zinc, as well as the other Group Ib elements such as silver and gold. Other pharmaceutically acceptable countercations that may be used include but are not limited to ammonium, other quaternary amines such as but not limited to choline, benzalkonium ion derivatives. As understood by those skilled in the art, the negatively charged diazeniumdiolate group must be counterbalanced with equivalent positive charge. Thus, referring to Formula 1, the valence number of the countercation or countercations ($R^2$) must match the stoichiometric number of diazeniumdiolate groups, both represented by y. In embodiments where more than one diazeniumdiolate is bound to the benzylic carbon, and $R^2$ is monovalent, $R^2$ can be the same cation or different cations.

$R^2$ can also be any inorganic or organic group covalently bound to the $O^2$—oxygen of the diazeniumdiolate functional group including but not limited to substituted or unsubstituted aryl groups, as well as a sulfonyl, glycosyl, acyl, alkyl or olefinic group. The alkyl and olefinic group can be a straight chain, branched chain or substituted chain. $R^2$ may be a saturated alkyl, such as, methyl or ethyl or an unsaturated alkyl (such as allyl or vinyl). Vinyl protected diazeniumdiolates are known to be metabolically activated by cytochrome P-450. $R^2$ may be a functionalized alkyl, such as, but not limited to, 2-bromoethyl, 2-hydroxypropyl, 2-hydroxyethyl or S-acetyl-2-mercaptoethyl. The latter example is an esterase sensitive protecting group. The former examples provide a chemical functional group handle. Such strategies have been successfully employed to link peptides to the diazeniumdiolate molecule. Hydrolysis may be prolonged by addition of the methoxymethyl protecting group. $R^2$ may be an aryl group, such as 2,4-dinitrophenyl. This type of protecting group is sensitive towards nucleophiles, such as glutathione and other thiols. It is obvious to those skilled in the art that several different protecting groups may be used, and/or the stoichiometry of the protecting group addition may be adjusted such that not all the diazeniumdiolate moieties are protected with the same protecting group, or not all the diazeniumdiolate groups are protected at all. By using different protecting groups, or varying the stoichiometry of the protecting group(s) to diazeniumdiolate ratio, the practitioner may engineer the release of NO to a desired rate.

$R^3$ is a phenyl group. The phenyl group may be pendant from the polymer backbone (as shown in Formula 2) or part of the polymer backbone (as shown in Formula 3). In non-polymeric embodiments $R^3$ may be a substituted or non-substituted phenyl group.

Any of a wide variety of polymers can be used in the context of the present invention. It is only necessary that the polymer selected is biologically acceptable. Illustrative of the polymers suitable for use in the present invention and used as the "Polymer", "Polymer$^1$", or "Polymer$^2$" (collectively "Polymer") in the general formulas include, but are not limited to: polystyrene; poly(α-methylstyrene); poly(4-methylstyrene); polyvinyltoluene; polyvinyl stearate; polyvinylpyrolidone; poly(4-vinylpyridine); poly(4-vinylphenol); poly (1-vinylnaphthalene); poly(2-vinylnaphthalene); poly(vinyl methyl ketone); poly(vinylidene fluoride); poly(vinylbenzyl chloride); polyvinyl alcohol; poly(vinyl acetate); poly(4-vinylbiphenyl); poly(9-vinylcarbazole); poly(2-vinylpyridine); poly(4-vinylpyridine); polybutadiene; polybutene; poly(butyl acrylate); poly(1,4-butylene adipate); poly(1,4-butylene terephthalate); poly(ethylene terephthalate); poly(ethylene succinate); poly(butyl methacrylate); poly(ethylene oxide); polychloroprene; polyethylene; polytetrafluoroethylene; polyvinylchloride; polypropylene; polydimethylsiloxane; polyacrylonitrile; polyaniline; polysulfone; polyethylene glycol; polypropylene glycol; polyacrylic acid; polyallylamine; poly(benzyl methacrylate); derivatized polyolefins such as polyethylenimine; poly(ethyl methacrylate); polyisobutylene; poly(isobutyl methacrylate); polyisoprene; poly (DL-lactide); poly(methyl methacrylate); polypyrrole; poly (carbonate urethane); poly[di(ethylene glycol) adipate]; polyepichlorohydrin; phenolic resins (novolacs and resoles); poly(ethyl acrylate); and combinations thereof including grafts and copolymerizations.

Polymer may also be represented by a styrenic resin, including, but not limited to: acrylonitrile butadiene styrene terpolymer; acrylonitrile-chlorinated polyethylene-styrene terpolymer; acrylic styrene acrylonitrile terpolymer; styrene acrylonitrile copolymers; olefin modified styrene acrylonitrile copolymers; and styrene butadiene copolymers.

Furthermore, Polymer may be represented by a polyamide, including, but not limited to: polyacrylamide; poly[4,4'-methylenebis(phenyl isocyanate)-alt-1,4-butanediol/di(propylene glycol)/polycaprolactone]; poly[4,4'-methylenebis(phenyl isocyanate)-alt-1,4-butanediol/poly(butylene adipate)]; poly[4,4'-methylenebis(phenyl isocyanate)-alt-1,4-butanediol/poly(ethylene glycol-co-propylene glycol)/polycaprolactone]; poly[4,4'-methylenebis(phenyl isocyanate)-alt-1,4-butanediol/polytetrahydrofuran]; terephthalic acid and isophthalic acid derivatives of aromatic polyamides (e.g. Nylon 6T and Nylon 61, respectively); poly(imino-1,4-phenyleneiminocarbonyl-1,4-phenylenecarbonyl); poly(m-phenylene isophthalamide); poly(p-benzamide); poly(trimethylhexamethylene terephthalatamide); poly-m-xylyene adipamide; poly(meta-phenylene isophthalamide) (e.g. Nomex); copolymers and combinations thereof; and the like.

Also, Polymer may be represented by polymers including, but not limited to: polyesters; polyarylates; polycarbonates; polyetherimides; polyimides (e.g. Kapton); and polyketones (polyether ketone, polyether ether ketone, polyether ether ketone, and the like); copolymers and combinations thereof; and the like.

Polymer may be represented by a biodegradable polymer including, but not limited to: polylactic acid; polyglycolic acid; poly(ϵ-caprolactone); copolymers; biopolymers, such as peptides, proteins, oligonucleotides, antibodies and nucleic acids, starburst dendrimers; and combinations thereof.

Polymer may also be represented by silane and siloxane mono- and multilayers.

Embodiments with Pendant Phenyl Groups

The pendant phenyl ring from the polymer may have substitutions. The substituted phenyl may be substituted with any moiety that does not interfere with the NO-releasing properties of the compound and maintains a covalent bond to the polymer backbone. Appropriate moieties include, but are not limited to, aliphatic, aromatic and non-aromatic cyclic groups. Aliphatic moieties are comprised of carbon and hydrogen but may also contain a halogen, nitrogen, oxygen, sulfur, or phosphorus. Aromatic cyclic groups are comprised of at least one aromatic ring. Non-aromatic cyclic groups are comprised of a ring structure with no aromatic rings. The phenyl ring may also be incorporated in multi ring systems examples of which include, but are not limited to, acridine, anthracene, benzazapine, benzodioxepin, benzothiadiazapine, carbazole, cinnoline, fluorescein, isoquinoline, naphthalene, phenanthrene, phenanthradine, phenazine, phthalazine, quinoline, quinoxaline, and other like polycyclic aromatic hydrocarbons. Additional moieties that can be substituted on the phenyl ring include, but are not limited to, mono- or di-substituted amino, unsubstituted amino, ammonium, alkoxy, acetoxy, aryloxy, acetamide, aldehyde, benzyl, cyano, nitro, thio, sulfonic, vinyl, carboxyl, nitroso, trihalosilane, trialkylsilane, trialkylsiloxane, trialkoxysilane, diazeniumdiolate, hydroxyl, halogen, trihalomethyl, ketone, benzyl, and alkylthio.

Polymers according to the present invention may be derived from commercially available chloromethylated polystyrene. Alternatively, chloromethylated polystyrene may be synthesized in a number of ways, including, but not limited to: utilizing chloromethyl alkyl ethers in the presence of Lewis acid catalysts (Merrifield, 1963); oxidation of poly(4-methylstyrene) using cobalt(III) acetate in the presence of lithium chloride (Sheng and Stover, 1997); or treatment of p-methylstyrene with sodium hypochlorite solution in the presence of phase transfer catalysts (Mohanraj and Ford, 1986; Le Carre et al., 2000).

In one preferred embodiment of the present invention, using Formula 2, a polymer may be synthesized in a two-step procedure as outlined in Scheme 1. In the first step (1), chloromethylated polystyrene is treated using methods known in the art to replace the —Cl atom with a nucleophilic substituent. It is desirable that the nucleophilic substituent activates the benzylic carbon protons for the introduction of diazeniumdiolate functional groups. In a preferred embodiment of this invention, the atom replacing the —Cl atom of the chloromethylated polystyrene is an electronegative heteroatom. It is preferred that the nucleophilic group replacing the —Cl atom is electron withdrawing. It is most preferred that the substituent be a cyano group. Additional preferred substituents may be selected from a group that includes —OR, —NR$_1$R$_2$, and —SR. The —OR group may be, but is not limited to, —OCH$_3$, —OC$_2$H$_5$, and —OSi(CH$_3$)$_3$. The replacing group may be a thiol group, such as, but not limited to, —SC$_2$H$_5$, and —SPh (where the Ph group is substituted or unsubstituted). The replacing group may also be a amine, such as, but not limited to, —N(C$_2$H$_5$)$_2$.

The second step (2) in Scheme 1 requires treatment of the polymer with a base in the presence of NO gas. The solvent for the reaction should not react with NO in the presence of a base (e.g. acetonitrile or ethanol). It is preferable that the selected solvent should swell the polystyrene. Suitable solvents include, but are not limited to, THF and DMF. Suitable bases include, but are not limited to, sodium methoxide and sodium trimethylsilanolate. In accordance with the method of the invention the resulting resin derived from chloromethylated polystyrene following these procedures will contain multiple —[N(O)NO]$^-$ functional groups which spontaneously release NO in aqueous media. The R$^2$ substituent referred to in the general Formulas and Scheme 1 represents a pharmaceutically acceptable counterion, hydrolysable group, or enzymatically-activated hydrolysable group as described above.

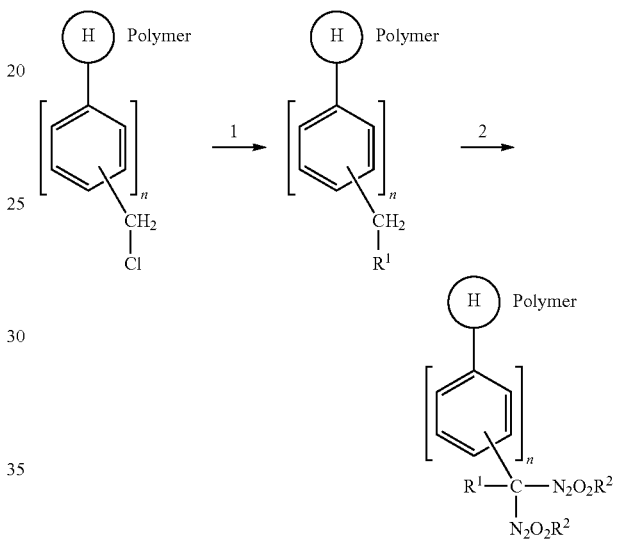

Scheme 1.

Embodiments Using Silane/Siloxane Polymers

In another preferred embodiment of the present invention, using Formula 2 where polymer is represented by a siloxane, a NO-releasing siloxane polymer may be synthesized in a similar procedure as outlined in Scheme 1 where the material is first coated with the silane/siloxane and then modified to an NO-releasing agent. A general description of surface preparation and silane/siloxane deposition is described below.

Surface Preparation

For the process of creating an embodiment of the present invention, an NO-releasing coating that is covalently bound to the substrate surface, it is critical to have a surface that presents pendant hydroxyl groups. As known to those skilled in the art, many surfaces can be easily modified (oxidized) to contain hydroxyl groups pendant to the surface. Such surface treatments include but are not limited to soaking in concentrated NaOH or KOH, or exposure to concentrated solutions of hydrogen peroxide (Srinivasan, 1988; Endo, 1995; Yoshida, 1999; Fitzhugh, U.S. Pat. No. 6,270,779; Kern, 1995.). The examples section will describe specific methodology for producing surface hydroxyl groups.

Once the surface is in the appropriate chemical form, the siloxane(s) coating can be deposited. For embodiments requiring dense, horizontal monolayers, trichlorosiloxane derivatives are preferred, and for thicker vertical coatings, alkoxysiloxane derivatives are preferred. Each embodiment requires a specific chemical methodology.

Formation of Monolayers

In embodiments of the present invention where dense monolayers of C-based diazeniumdiolate coatings are preferred, deposition of the commercially available 4-cyanomethylphenyl triethoxysilane, 4-chloromethylphenyl trichlorosilane, or any trichlorosilane that contains a pendant methylphenyl group where the benzylic carbon can be substituted with any group which allows for substitution of diazeniumdiolate functional groups on the benzylic carbon atom is preferred. For embodiments where the cyano-substituted benzylic carbon is desired, it is preferred to deposit the commercially available 4-cyanomethylphenyl triethoxysilane on the surface. For all other embodiments, it is preferred to deposit the commercially available 4-chloromethylphenyl trichlorosilane onto the surface, and, at a subsequent step, substitute the chloro atom for the desired substituent using the appropriate nucleophile as described in the "Substituting a Nucleophile" section below. This method eliminates the need for potentially complicated synthesis of trichlorosiloxane derivatives with the desired benzylic carbon substituent. It should be noted that it is possible to use a trialkoxysilane under similar conditions to produce a monolayer (Bierbaum, 1995), however the high reactivity of the trichlorosiloxane derivatives to what is a very minimal amount of surface water causes the trichloro derivatives to be preferred for monolayer applications.

Typically, the trichlorosilanes are deposited using anhydrous conditions, using a 0.1-3% trichlorosilane solution in a hydrocarbon solvent such as toluene or hexadecane under an inert atmosphere. The application of the trichlorosilane solution can be applied to the desired surface under anhydrous conditions and an inert atmosphere via a variety of methods including but not limited to dipping, vapor deposition, spray coating, flow coating, brushing and other methods known to those skilled in the art. The polymerization is usually complete from 1 to 24 hours. The material is then rinsed with a hydrocarbon solvent, heat cured at 110° C. for 20 to 60 min to form covalent bonds with the surface hydroxyls as described below, and prepared for further use. While not wishing to be bound to any particular theory, the monolayer is formed as follows. The water necessary for the polymerization of the trichlorosilane derivatives is provided by the intrinsic water found on the surface of most substrates. Because this inherent surface water is the only available water to drive the polymerization reaction, the polymerization of the silane derivatives can only occur at the surface of the material. Thus, the localization of water to the surface limits the polymerization to a surface monolayer and only trichlorosilane molecules contacting the solid surface are hydrolyzed, producing a closely packed monolayer. Too much water, such as where rigorous anhydrous conditions in the solvent are not observed, will lead to rapid polymerization of the silanes, possibly before they have even had a chance to deposit on the substrate surface (Silberzan, 1991). In comparison, hydrolysis of alkoxysilanes in 95% alcoholic solutions results in significant oligomerization of the silanes before the substrate to be coated is introduced into the solution. Numerous reports support this scheme (Ulman, 1996; Sagiv, 1980; Wasserman, 1989; Bierbaum, 1995).

It should be noted, and is known by those skilled in the art, that this process of monolayer deposition can be repeated using multiple applications of trichlorosilane derivatives, resulting in the ability to build many subsequent monolayers (Tillman, 1989).

Formation of Three Dimensional Networks

In embodiments of the present invention where thicker, more vertically polymerized C-based diazeniumdiolate coatings are preferred, the alkoxysilane class of siloxane is preferred. The appropriate alkoxysilanes, such as but not limited to cyanomethylphenyl alkoxysilane derivatives, chloromethylphenyl alkoxysilane derivatives, or any alkoxysilane derivative capable of permanently entrapping a chloromethylphenyl or cyanomethylphenyl group within its matrix is preferred. Generally, a 95% ethanol 5% water solution is adjusted to pH 5±0.5 with acetic acid and the appropriate alkoxy silane is added to a concentration between 1 and 10% (v/v). During the next several minutes, the alkoxysilane derivatives will undergo hydrolysis to form silanols which will condense to form oligomers. At this point the substrate can be dipped, or otherwise coated according to methods known to those skilled in the art. While not wishing to be bound to any particular theory, the silanols condense into larger oligomers which hydrogen bond to the surface hydroxyls of the substrate and can reach out like 'hairs' on the surface. The siloxane(s) continue to polymerize and form vertical matrices. The duration of exposure of the substrate to the alkoxysilane derivative is generally proportional to the thickness of the coating formed. At the desired time point, the coated material is rinsed with ethanol, heat cured at 110° C. for 20 to 60 min if desired, and prepared for further use.

The appropriate methylphenyl siloxane derivative may be used pure or in any fraction with other siloxane(s) to form the coating, as well as with other compatible polymers.

Once the desired siloxane coating has been deposited, the formation of covalent bonds between the coating and the oxidized substrate surface can be achieved. This is accomplished through the application of dry heat, typically but not exclusively at 110° C. for 20 to 60 min. Without being bound by any particular theory, under the conditions typical to applying dry heat, the hydroxyl moieties in the siloxane coating that are hydrogen bonded to the hydroxylated surface of a substrate will react through a dehydration reaction and form strong covalent silicon-oxygen bonds.

Substituting a Nucleophile

In the case where cyanomethylphenyl siloxanes are used in the coating step, the addition of a nucleophile to the benzylic carbon is not necessary, as the cyano group is an excellent activating group. Use of cyanomethylphenyl siloxanes allows the practitioner to go directly to the diazeniumdiolation step. If a chloromethyphenyl siloxane or other chloromethyphenyl derivative is used, or the practitioner desires to change the nucleophile, thereby changing the characteristics of the diazeniumdiolate group and thus altering the rate of release of NO from the coating, the chloro group must be exchanged with a nucleophile that allows for the introduction of the diazeniumdiolate group as described above. This step is performed as follows: The coated substrate is immersed in a solution of DMF containing a catalytic amount of potassium iodide and the nucleophile of choice. The solution is heated to 80° C. for up to 24 hours. During this time the substitution reaction occurs. The substrate is then removed from the solvent, washed with fresh DMF and blown dry with nitrogen or left in air to dry.

Diazeniumdiolation Step

Once the appropriate nucleophile is added to the benzylic carbon of the appropriate siloxane derivative, the coated material is placed in a Parr pressure vessel containing a solvent such as THF, DMF or MeOH. A sterically hindered base such as sodium trimethylsilanolate is added. The choice of base is important because the silicon-oxygen bonds of the siloxane network are sensitive to aggressive nucleophiles such as hydroxides and alkoxides. The vessel is purged of atmosphere with an inert gas and pressure checked before exposure to several atmospheres pure NO gas. After 1 to 3 days, the coated materials are removed, washed and dried in air before storage under argon at 4° C.

Embodiments with Polymeric Backbone Comprising Phenyl Groups

The polymeric NO releasing resin described in various examples above has the —[N(O)NO]⁻ functional groups pendant to the polymeric backbone. The present invention also provides methods to modify any phenyl ring found in the backbone of the polymer. Thus, other means to introduce the nucleophile to obtain the molecular arrangement shown in Formula 1 are considered within the scope of the present invention.

Considering Formula 3, Polymer$^1$ and Polymer$^2$ may be equivalent or different from each other, and may include but not be limited to: polybutylene terephthalate; polytrimethylene terephthalate; and polycyclohexylenedimethylene terephthalate. In addition, aramides (a class of polymers in the nylon family synthesized from the reaction of terephthalic acid and a diamine) may also be represented by Polymer$^1$ or Polymer$^2$. Examples of such aramides include, but are not limited to, poly(p-phenylene terephthalamide) and poly(m-phenylene isophthalamide). As in other embodiments of this invention described above, it is desirable that the nucleophilic substituent activates the benzylic carbon protons for the introduction of diazeniumdiolate functional groups.

In a preferred embodiment, the atom replacing the —Cl atom of the chloromethylated polystyrene is an electronegative heteroatom. It is preferred that the nucleophilic group replacing the —Cl atom is electron withdrawing. Preferred substituents for R$^1$ may be represented by, but are not limited to: a cyano group; an ether group, such as, but not limited to —OCH$_3$, —OC$_2$H$_5$, and —OSi(CH$_3$)$_3$; a tertiary amine; and a thioether, such as, but not limited to, —SC$_2$H$_5$, and —SPh (where the Ph group can be substituted or unsubstituted). The R$^1$ group may also be a amine such as, but not limited to, —N(C$_2$, H$_5$)$_2$.

Polyethylene terephthalate (PET) is used in an exemplary embodiment of the present invention, where Polymer$^1$ and Polymer$^2$ in Formula 3 represent the repeating ethyleneterephthalate structure. Condensation of terephthalic acid and a diol such as ethylene glycol results in the polyester. Other examples of polyesters can be produced by variation of the diol. Such polyesters may be transformed into NO-releasing materials in a four step process.

By way of example and not in limitation, as shown in Scheme 2, the aromatic ring contained in a polymer of PET may be treated with formaldehyde and acetic acid to produce a benzyl alcohol (Yang, 2000). Treatment with tosyl chloride introduces an effective leaving group onto the polymer. Further treatment with a nucleophile of choice will displace the tosylate and provide the necessary structure for introduction of the —[N(O)NO]⁻ functional group. Therefore, it should be apparent to one of ordinary skill in the art that there may be a wide variety of polymers containing an aromatic phenyl group which may be modified to contain the necessary chemical structure for transformation into a carbon-based diazeniumdiolate through the teachings of the present invention.

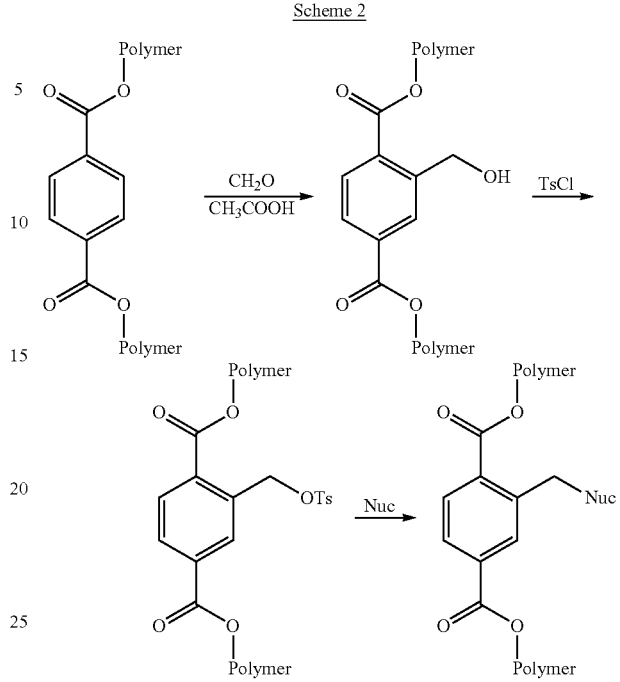

Scheme 2

General Chemistry and Strategies to Control Release of NO

Without restraint to any one theory, the importance of the benzylic structure (methylphenyl group) to the invention is threefold. First, the benzylic carbon has relatively acidic protons and the choice of nucleophile should increase the acidity of the benzylic protons such that a base can easily extract a proton. Exposure of benzylic compounds to NO gas in the absence of base is not known to produce the diazeniumdiolate functional group. Secondly, the aromatic ring resonance stabilizes the carbanion formed by extraction of a proton by base. The stabilized carbanion allows for the reaction of the carbanion with NO, to produce a radical carbon center and nitroxyl anion (NO⁻). Further reaction of the radical carbon center with NO or NO dimer produces the diazeniumdiolate functional group. The anionic diazeniumdiolate functional group enhances the acidity of the last benzylic proton and allows an additional diazeniumdiolate group to be added to the carbon. In this manner, up to three diazeniumdiolate functional groups are introduced into the polymer via the benzylic carbon. Thirdly, the presence of resonant electrons in the aromatic ring helps promote spontaneous decomposition of the —[N(O)NO]⁻ group in aqueous media. Other bisdiazeniumdiolates, namely methylene bisdiazeniumdiolate [H$_2$C(N$_2$O$_2$Na)$_2$] lack resonant electronic forces that participate in the decomposition process and thus show remarkable stability (inability to release NO) in solution (Traube, 1898).

Figure 2:
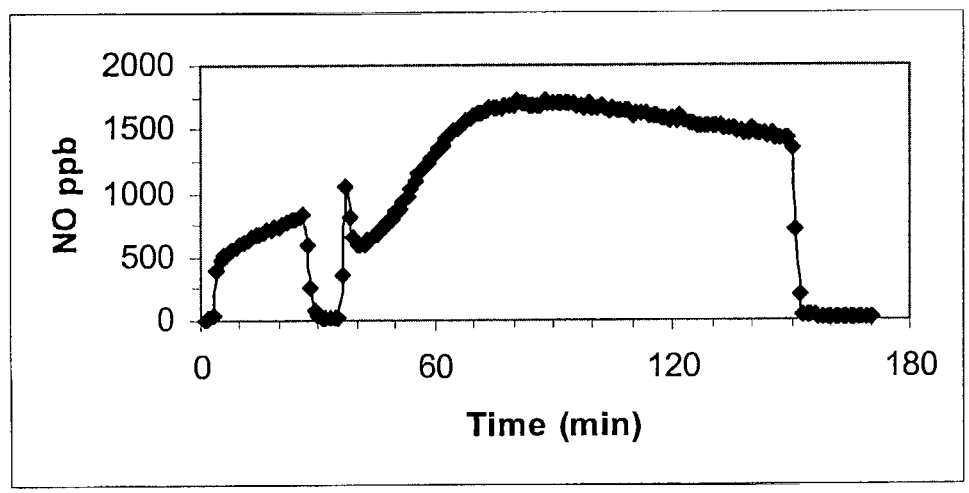
FIG. 2 shows the quantity of NO-release from ethoxy-modified chloromethylated polystyrene diazeniumdiolate. This polymer composition was packed in 4 mm dialysis membrane (MWCO 3500), placed in a reactor vessel and submerged in pH 7.4 buffer. After 26 minutes the dialysis tube was removed to demonstrate the absence of NO-releasing leachable materials. At 35 minutes, the tube was reinserted into the reactor vessel and NO was released over the next 2 hour period, producing NO at a rate of 5.3×10⁻¹¹ moles NO/mg resin/min.

In addition to their advantage of releasing NO under physiological conditions without forming nitrosamine carcinogens, the degree and rate of NO release of these polymeric materials may be engineered using several types of manipulations. FIGS. 1 and 2 show the NO release profiles of two different C-based NO releasing head groups attached to methyl polystyrene. The structural differences in the NO-releasing headgroup were achieved by changing the nucleophile that results in the R$^1$ substituent. The release profile in FIG. 1 is the result of a cyano-modified (R$^1$) benzylic carbon and FIG. 2 shows an ethoxy-modified (R$^1$) benzylic carbon. Examination of the Figures indicates the cyano-modified polymer exhibits a rapid release profile, whereas the ethoxy-modified polymer exhibits a prolonged but less robust release of NO. Several more examples of the results of manipulation of $R^1$ on NO release properties are described in the Examples. It should be apparent to one skilled in the art that a contiguous polymer may contain more than one type of nucleophilic substituent. As shown in Scheme 3, chloromethylated polystyrene cross-linked with divinylbenzene can be modified with two different nucleophiles, $R^1_a$ and $R^1_b$, to produce two different types of NO-donor moieties. The ability to control the release rate of NO through manipulation of $R^1$ allows for precise engineering of the release of NO from the polymer on a macro scale.

Scheme 3

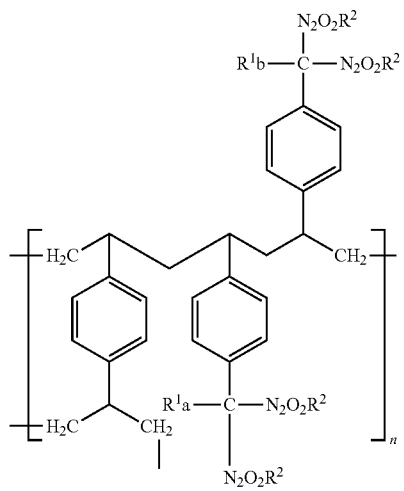

Another preferred way of reaching the desired amount and rate of NO release on a macro scale is to blend two or more of the individually synthesized polymers together to achieve the desired rate of NO release from the polymer. This method has the advantage over manipulating $R^1$ in the NO-releasing headgroups of a single polymer because it eliminates the need for stoichiometric control of the synthetic chemistry to achieve the desired release rate. However, this method may not be easily amenable to micro- and nano-scale applications.

An additional way to affect the rate and degree of NO release from the polymer, one which especially holds relevant for the polystyrene-based polymers, is to vary the degree of cross-linking of the polymer. Generally, a lesser degree of cross-linking provides a more porous polymeric structure. While this does not change the degree of nucleophilic substitution and diazeniumdiolation, it provides a more rapid and greater degree of NO release from the polymer because the active NO-releasing sites are more accessible to the aqueous solvent. Increasing the polymer cross-linking decreases the porosity of the polymer, which serves to inhibit aqueous solvent access. Highly cross-linked polymers release NO for longer periods of time (see, for example, U.S. Patent Application Pub. No.: US 2003/0077243 A1). Thus, various rates of NO-release may be obtained by controlling the access of aqueous solution to the —[N(O)NO]⁻ functional groups through the degree of cross-linking of the polymer.

The C-based diazeniumdiolate polymer of the present invention is also an improvement over the prior art in terms of time of synthesis and amount of NO generated. For example, according to the teachings of U.S. Pat. No. 5,405,919, a polyamine was linked to chloromethylated polystyrene and a slurry of the aminopolystyrene in acetonitrile was subsequently exposed to NO to produce a N-based diazeniumdiolate. However, such a N-based diazeniumdiolate required a week to synthesize and produced very low levels of NO under physiological conditions which is not useful for many applications. The method of the present invention utilizes a suitable solvent to swell the resin and adding potassium iodide as a catalyst to accelerate the nucleophilic substitution reaction, which is a significant improvement over the reaction time (2 days versus 8 days) and NO-release levels (ppm NO versus very low levels) when compared to that disclosed in U.S. Pat. No. 5,405,919.

Polymers that release NO are desirable for providing localized fluxes of NO at the specific target sites. The NO may be localized in vivo, used in ex vivo applications of cells, tissues, and organs, or as in vitro reagents. In applications where NO is applied to cells in culture, the use of polymeric materials provide a distinct advantage in that they are easily separated from the cell suspension due to their size and/or density.

Polymeric forms of diazeniumdiolate nitric oxide donors can be used to provide localized delivery of nitric oxide, and therefore are useful in devices such as stents, prostheses, implants, and a variety of other medical devices. Polymeric materials may also be used in in vitro and ex vivo biomedical applications.

Use of the Present Invention in Coatings for Medical Devices

The present invention provides methods for a novel class of coatings in which NO-releasing carbon-based diazeniumdiolates may be covalently linked to a surface, whereby the release of NO imparts increased biocompatibility or other beneficial properties to the coated surface. In order for NO to be therapeutic it is most preferable that it be delivered/produced at the site of interest. The polymers described herein have the potential to generate NO temporally and spatially at the desired area of interest. Thus, a medical device comprised of the NO-releasing polymers may provide a localized flux of NO without any deleterious systemic effects such as hypotension. The beneficial physiological properties of NO may be targeted directly at desired site of application. The structural and physical characteristics of the NO-releasing polymers in the present invention may be manipulated to suit the treatment of the biological disorder. The polymers may take the form of a device such as an arterial stent, vascular graft, patch, or implant. The NO-releasing polymers may also be microencapsulated or enteric coated for ingestion. In addition, the NO-releasing polymers of the present invention may be incorporated into other polymeric structures by co-polymerization, precipitation or deposition as practiced by those skilled in the art.

As one skilled in the art would appreciate, exemplary embodiments of the present invention find utility in a wide variety of applications depending upon the physiological disorder. One possible preferred application for this class of coatings would be in medical devices where the surface can be comprised of but is not limited to metals including titanium, alloys of titanium including $Ti_6Al_4V$ and nitinol, niobium, molybdenum, chromium, aluminum, nickel, copper, gold, silver, platinum, vanadium, all alloys and combinations thereof, all varieties of stainless steel including surgical grade, and any metal capable of forming surface oxide groups; silicates including but not limited to glass, fused silica glass, 96% silica glass, aluminosilicate glass, borosilicate glass, lead glass, soda lime glass; polymers comprised of but not limited to silastic, hydroxylated polyolefins, or any plastic or polymeric material with pendant surface hydroxyl groups, including biopolymers.

Vascular Stents

Each year in the U.S. about 700,000 patients suffering from coronary atherosclerosis, blockage or narrowing of the arteries to the heart, undergo percutaneous transluminal coronary angioplasty (PTCA) as a means to return normal circulation to the heart. This procedure involves the inflation of a balloon catheter in the narrowed area of the coronary artery thus enlarging the diameter and increasing the blood flow to the affected area. However, approximately 30-50% of the time, the arterial occlusion returns in a process termed restenosis. A preventive measure following PTCA is the deployment of a vascular stent to act as a support in the artery. Despite this treatment, restenosis still occurs in 15-25% of patients receiving stents and additional treatment is required.

The current state of the art vascular stents are designed to elute anti-proliferative medications such as sirolimus as a means to inhibit restenosis. However, these drugs are not antithrombotic and patients have developed life threatening blood clots. Furthermore, the anti-proliferative drugs inhibits the growth of vascular endothelial cells, which are beneficial to the post angioplasty healing process. The anti-proliferative drug-eluting stent exemplifies a fundamental problem underlying the development of drug-eluting stents. There is no single drug that stands out as an effective treatment for this disease.

An alternative approach towards treating restenosis is to incorporate a natural product that inhibits platelet aggregation, prevents smooth muscle cell proliferation and promotes re-endothelialization of the injured vessel and endothelialization of the stent surface. Nitric oxide (NO) can perform these physiological functions. A vascular stent can be coated with the present invention to elute therapeutic amounts of NO which would accelerate the healing process following PTCA stent deployment thus improving patient outcome over the current state of the art drug eluting stents.

By way of example and not limitation, a cardiovascular stent comprised of or coated with the NO-releasing polymers of the present invention will possess the ability to resist platelet adhesion, prevent platelet aggregation, inhibit vascular smooth muscle cell proliferation (Mooradian et al., 1995), and stimulate the proliferation of vascular endothelial cells. The current state of the art anti-proliferative eluting stents do not inhibit blood clot formation. Patients receiving these stents must maintain a 3-month regimen of anti-clotting medication. Recent reports disclose the detection of blood clots in dozens of patients who have received this type of stent (Neergaard, 2003). One skilled in the art can utilize a coating that releases both the anti-proliferative drug and NO simultaneously.

The proliferation of endothelial cells (ECs) by NO is of great interest because it is the first step towards neovascularization (Ausprunk, 1977). If NO can stimulate EC proliferation then an inserted medical device such as a vascular stent or graft modified with a NO-releasing coating of the present invention might be able to promote overgrowth of the device with endothelial tissue. In this way, blood contact with the device will move from the NO-releasing coating to a natural cellular layer. Recently, a group has genetically engineered endothelial cells to over-express endothelial nitric oxide synthase (eNOS) in an attempt to enhance the EC retention on a vascular graft (Kader, 2000).

Other Vascular Devices

The various beneficial effects of NO in the cardiovascular system can be further exploited using the present invention. One skilled in the art will realize that the anti-platelet effect will be useful when applied as a coating to vascular grafts or when the polymers of the present invention are formed into vascular grafts. The NO-releasing polymer will give off sufficient NO for sufficient duration to eliminate blood clotting events from occurring until the graft can be overgrown with endothelial cells.

One skilled in the art will also realize that polymers from the present invention can be used in extracorporeal membrane oxygenation circuits (ECMO), more commonly known as a "heart/lung machine." A major complication of this procedure is the loss of platelets due to adhesion along the inner surface of the tubing used to form the extracorporeal circuit. A thromboresistant surface made from N-based diazeniumdiolate small molecules embedded in a polymer matrix reduced the loss of platelets in a rabbit model of ECMO (Annich et al., 2000). However, the polymer in the study has the disadvantages associated with N-based diazeniumdiolate polymers (i.e., potential carcinogen). Polymers of the present invention do not have the associated toxic potential of the N-based diazeniumdiolates.

Another beneficial application of the present invention is for patients undergoing hemodialysis. Application of the present invention to shunts used for hemodialysis, extracorporeal tubing, and the dialysis membrane itself can be used to decrease the adhesion of platelets to the surfaces, resulting in increased circulating platelets in the patient.

Additional applications of the present invention include but are not limited to increasing the patency of percutaneous needles, increasing the thromboresistance of indwelling sensors and surgical tools, engineering the formation of new blood vessels, treating hypertension, and other applications were localized therapeutic levels of NO would be beneficial to the patient.

Indwelling Catheters

An endemic problem associated with hospitalization is manifested in the number of infections and deaths directly related to inserted medical devices such as catheters, shunts, and probes. It is estimated that up to 20,000 deaths occur each year due to infection acquired from vascular catheterization. The inserted medical device provides direct access into the body for advantageous skin microorganisms. These bacteria adhere to and colonize upon the inserted device and in the process form an antibiotic resistant matrix known as a biofilm. As the biofilm grows, planktonic cells can break free and spread the infection further into the patient. In order to prevent infection, the inserted medical device must prevent the biofilm formation. This can be done by killing the bacteria before they can colonize the medical device or prevent the adhesion of bacteria to the device such that a biofilm cannot form.

It is well known that NO can prevent blood platelets from adhering to various surfaces and NO has antimicrobial properties. A recent report demonstrates that NO can also inhibit bacterial adhesion (Nablo et al, 2001). Polyaminosiloxanes were deposited on glass slides and derivatized into NO donors. *P. aeruginosa* adhesion was inhibited in a dose dependent manner by the NO-releasing sol-gels. This early report strongly suggests that bacterial adhesion can be influenced by surfaces designed to release NO. Therefore, catheters coated with NO-releasing polymers of the present invention may inhibit biofilm formation and improve patient health care.

Contact Lens Cases

Contact lens-related eye infections impact millions of people yearly. Standard guidelines for lens care can minimize eye infection, but it has been shown that only about 50% of lens wearers adhere to appropriate guidelines. Among contact lens wearers that do follow the recommended guidelines, lens-related infections still occur. During usual use and storage procedures, microorganisms adhere to contact lenses.

Daily lens cleaning removes most of these microorganisms; however, microbes can establish biofilms on lenses. Often such biofilms are not satisfactorily removed despite disinfection and cleaning with systems currently available. In many cases the source of the microorganisms is the lens case (McLaughlin et al. 1998). Even for non-symptomatic lens wearers, the lens case contains bacterial biofilms, and this source most likely serves as an important contamination route for lenses, despite the use of disinfectants and cleaning solutions (McLaughlin et al. 1998). In addition, biofilms formed by pathogenic organisms are of increasing clinical importance due to their resistance to antibiotics and host immune responses, as well as their ability to develop on indwelling medical devices.

Use of the Present Invention in the Manufacture of Medical Devices

In addition to the ability to coat medical devices, the present invention also provides a method to manufacture devices or components of devices using NO-releasing polymers. Many of the exemplary embodiments of the present invention, use of such starting materials as, but not limited to, PET, PS, siloxane-based polymers, all of which can be used to manufacture entire medical devices or components thereof.

NO-releasing polymers of the present invention may be synthesized and extruded, molded, injection molded, blow molded, thermoformed or otherwise formed into complete devices or components thereof using methods known to those of skill in the art to produce solid devices or device components that release NO and comprise a medical device.

In an alternative method, the device or device components are manufactured using an appropriate non-NO-releasing polymer, and modifying the device or device components to release NO as described in Example 8.

Use in Platelet Storage Applications

One non-limiting example of the utility of NO-releasing polymers is in the ex vivo inhibition of platelets. Nitric oxide has been shown to be a potent inhibitor of platelet aggregation (Moncada et al., 1991). Application of NO to platelets also results in a decreased intracellular calcium response to agonists (Raulli, 1998) as well as other intracellular processes dependent on calcium, such as release of granule contents (Barrett et al., 1989). Example 12 shows the ability of NO-releasing polymers to inhibit agonist-induced platelet aggregation.

This ability of NO-releasing polymers to inhibit platelet activation ex vivo may be of considerable utility in the treatment of Platelet Storage Lesion (PSL). Platelet Storage Lesion is defined as the sum of the changes that occur in platelets following their collection, preparation, and storage (Chrenoff, 1992), and is responsible for the loss of platelet functionality that increases with increased duration of storage. These changes include cytoskeletal and surface antigen structural changes, release of dense and alpha granule contents, release of lysosomal contents, loss of membrane integrity, and defects of metabolism (Klinger, 1996). The mechanism(s) that cause PSL are poorly understood, but a general consensus is that PSL is related (at least partially) to the results of platelet activation during the storage period (Snyder (ed), 1992). Because NO is a known inhibitor of platelet activation (Moncada et al., 1991) and activation of storage granules (Barrett et al., 1989), treatment of stored platelets with NO-releasing agents may reduce the degree of PSL, resulting in an increased activatable platelet count, e.g., platelets that have their alpha and dense granules intact, decreased cellular debris, decreased autocoid concentration of the storage plasma, and decreased morphological changes that may affect platelet performance.

One skilled in the art can devise a number of ways to treat stored platelets with NO-releasing polymers. An exemplary embodiment of the present invention uses a carbon-based nitric oxide-releasing polymer that is manufactured pre-loaded within the blood storage compartment. The polymer should be of appropriate quantity and release rate to partially or completely inhibit platelet activation for a specified amount of platelet-rich plasma (PRP), platelet concentrate (PC), apheresed platelets (APP), or other platelet product that would be traditionally stored. The polymer should release inhibitory levels of nitric oxide for sufficient duration to cover the entire predicted duration period for the platelet product, although paradigms can be envisioned where the inhibitory flux of nitric oxide need not be present for the entire duration of storage.

The NO-releasing polymer may be a single entity or a blend of polymers designed to reach an optimized release rate and duration of NO release. Furthermore, the polymer may be designed to maximize its surface area, without interfering with platelet agitation within the platelet storage container. Also, the polymer may be anchored to the storage container, free, or contained within a permeable or semi-permeable membrane comprised of any material that is compatible with blood cells and blood plasma. Free polymer embodiments should be of an appropriate size and shape so as not to enter or clog the exit port that delivers the blood product to the recipient. Preferred embodiments would use, but not be limited to, polymers comprised of pendant carbon-based diazeniumdiolate groups. One skilled in the art would appreciate that NO-releasing polymers could be part of a complete manufactured system for platelet storage as described in U.S. Provisional Patent Application No. 60/471,724, Raulli et al., Systems and Methods for Pathogen Reduction in Blood Products.

The use of NO-releasing polymers of the present invention may also be useful in other applications as a platelet inhibitor. It is well known that exposure of human platelets to cold temperatures results in a "cold-induced" activation characterized by an immediate rise in platelet intracellular calcium levels (Oliver et al. 1999), and changes in morphology (Winokur and Hartwig, 1995). Recent studies describe a method to freeze-dry platelets (U.S. Pat. No. 5,827,741 Beattie et al.). The freeze-dried and reconstituted end product shows a 15 to 30% degradation of the viable platelet count (Wolkers et al. 2002). This may be due to a cold-induced activation of platelets during the initial lyophilization process, or the result of the thawing process. Exposure of the platelets to NO-releasing polymers of the current invention prior to, during, or after the lyophilization process may decrease or eliminate any cold-induced activation, and consequently may increase the viability of the freeze-dried platelets.

One skilled in the art can develop a variety of methods to incorporate C-based NO-releasing polymers of the present invention into methods for cooling, freezing, or freeze-drying platelet preparations. An exemplary embodiment would be similar to those described above for inhibition of stored platelets.

Use in Pathogen Reduction of Stored Human Platelets

It has been well established that nitric oxide can kill a variety of bacterial, fungal and viral pathogens (DeGroote and Fang, 1995). An exemplary embodiment of the current invention uses a nitric oxide-releasing polymer within the blood storage compartment that delivers sufficient levels of nitric oxide to reduce or eliminate viable microbes that may be contaminating the blood product (U.S. Provisional Patent Application No. 60/471,724, Raulli et al., Systems and Methods for Pathogen Reduction in Blood Products). Example 13 shows the ability of NO-releasing polymers to pathogens in blood storage containers.

The polymer will release sufficient levels of nitric oxide at an appropriate rate and for sufficient duration to kill, inactivate, or retard the further growth of pathogens that contaminate the blood product. Further, the polymer is comprised of material that is compatible with blood cells and blood plasma. The polymer may also be designed to maximize its surface area, without interfering with platelet agitation in the case of a platelet storage container. In exemplary embodiments, the polymer may be anchored to the storage container, free floating, or contained within a permeable or semi-permeable membrane comprised of any material that is compatible with blood cells and blood plasma. Free floating polymer embodiments should be of an appropriate size and shape so as not to enter or clog the exit port that delivers the blood product to the recipient. Preferred embodiments would use polymers comprised of pendant C-based diazeniumdiolate groups.

Use in Perfusion of Organs and Tissues for Treatment of Ischemia, Preservation, and Transplantation Nitric oxide has a potent and profound vasodilatory effect on mammalian blood vessels (Palmer et al., 1989). This pharmacological property, as well as the chemical antioxidant property of NO (Espey et al., 2002) make NO useful in transplantation medicine. When applied to the perfused organ, nitric oxide, acting as a vasodilator, allows greater perfusion of the deep tissues of the organ, bringing oxygen and nutrients to the tissue. The deeper penetration of the perfusate also benefits the organ in bringing more NO to the deep tissues, further enhancing the antioxidant ability of nitric oxide to prevent the oxidative damage typical of reperfusion injury (Ferdinandy and Schultz, 2003; Wink et al., 1993 and references therein).

While numerous types of NO donors are effective as vasodilators, many, like sodium nitroprusside (Kowaluk et al., 1992) and nitrosothiols (Dicks et al, 1996), require metabolic activation making them less predictable. This is especially relevant given the fact that the perfusate may not contain the necessary factors required for activation of these compounds as compared to blood. In the case where tissue thiols or metals are required for activation, the tissue itself may be unpredictably deficient or rich in these factors due to the effects of ischemia-related insult. Furthermore, these NO donors do not release the preferred antioxidant species (NO.), or need additional factors such as Cu to convert the release species to NO.. Finally, sodium nitroprusside (SNP), a common NO-releasing vasodilator, may give off cyanide after donating its NO. Such problems highlight some of the advantages of exemplary embodiments of the current invention, namely that a device gives off only NO and there are no spent donor molecules present in the perfusate.

The redox state of the released NO may be of particular interest. Many NO donors such as SNP release nitrosonium ion ($NO^+$) and some produce nitroxyl ion ($NO^-$). Both species have been shown to exacerbate the effects of reactive oxygen species (ROS), which are the agents that ultimately cause the oxidative tissue damage in ischemia reperfusion injury. The nitric oxide species released by the current invention is NO., which has been shown to counteract the ROS (Wink et al, 1996).

The ability of the polymers of the current invention to spontaneously and predictably release NO. represents an advantage over soluble NO donors as potential treatments in the organ perfusion process. This "donorless" delivery of NO is possible because the NO-releasing headgroup and the polymeric matrix to which it is attached remain insoluble when in standing or flowing aqueous solutions, while maintaining their ability to release soluble NO into the solution. In addition to the inherent advantages of the current invention to deliver a preferred antioxidant redox species of NO, this donorless approach eliminates the problem of circulating spent donor molecules.

Figure 3:
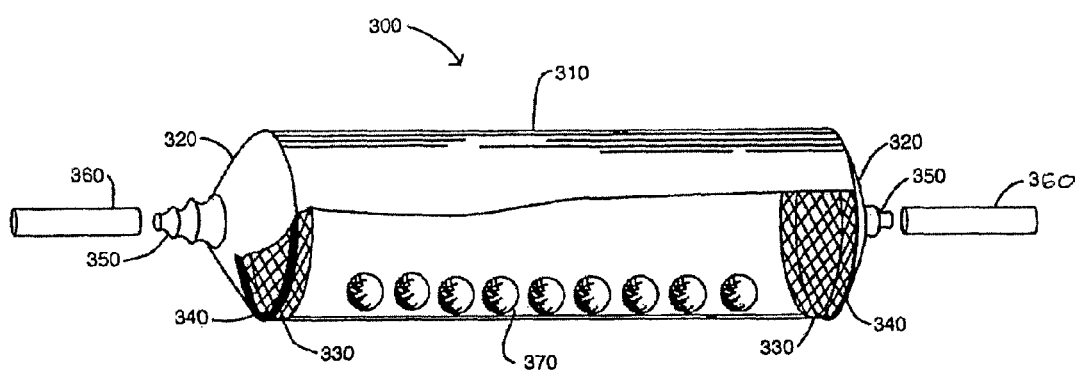
FIG. 3 illustrates a cut-away view of one embodiment of a device for delivering nitric oxide to a flowing perfusate.

Polymer(s) according to the present invention may be contained in an in-line device, whereby the flow of the perfusate through the device releases sufficient NO into the perfusate as to result in vasodilation of the organ vasculature and a neutralization of ROS in the perfused organ. An exemplary, but not limiting, embodiment is shown in FIG. 3. The device 300 includes a chamber 310, which could be cylindrical or other appropriate shape. Chamber 310 is closed at both ends using fritted discs 330, which self-seal or seal with a gasket 340. Cylindrical chamber 310 is capped at each end by a funnel-shaped collector 320 that channels fluid into a smaller nozzle 350, allowing for facilitated attachment to a perfusion line 360 on each end of the device 300.

Contained within chamber 310 is a solid polymer 370, according to the present invention. Polymer 370 may be of any desirable shape, may be attached to the wall of chamber 310 or otherwise anchored, or free within the chamber. The size of polymer 370 may also vary. However polymer 370 must be of a size that will be easily contained by fitted discs 330 on either end of chamber 310. It is preferable that the density of polymer 370 within chamber 310 is such as to allow free flow of the perfusate through device 300.

Also, a mesh size of fritted discs 330 should also be optimized to allow free flow of perfusate. One skilled in the art would appreciate that the size of chamber 310 may have an impact on the levels of NO released into the perfusate for any given flow rate, as the larger a chamber for a given flow rate the longer the exposure of the perfusate to the NO-releasing polymer will be, resulting in more NO dissolved in the perfusate. One having ordinary skill in the art may appreciate that the size, shape and geometry of the device 300 is merely exemplary and may be readily changed and remain effective in releasing NO within a perfusate. All such variations are within the scope of the present invention.

Example 14 demonstrates an ability of polymers according to the present invention to deliver significant quantities of NO to buffers flowing through an in-line container comprised of a fritted chamber with NO-releasing polymer contained within the chamber. The amount of NO contained in the effluent is one to two orders of magnitude greater than the concentration of NO required to achieve a vasodilatory effect in tissue bath experiments using aortic strips (Morley et al. 1993).

One skilled in the art would also appreciate that the compounds of the present invention could be part of a complete manufactured system for portable sterilization as described in U.S. Provisional Patent Application Nos. 60/534,395; 60/575,421; and 60/564,589, each of which are hereby incorporated by reference in its entirety.

Use as a Pharmaceutical Agent

A number of suitable routes of administration may be employed for treatment of animals, preferably mammals, and in particular in humans to provide an effective dose of nitric oxide using the current invention. Oral and rectal dosage forms are preferred. However, it is possible to use subcutaneous, intramuscular, intravenous, and transdermal routes of administration. Of the possible solid oral dosage forms, the preferred embodiments include tablets, capsules, troches, cachets, powders, dispersions and the like. Other forms are also possible. Preferred liquid dosage forms include, but are not limited to, non-aqueous suspensions and oil-in-water emulsions.

In one embodiment of a solid oral dosage form, a tablet includes a pharmaceutical composition according to the present invention as the active ingredient, or a pharmaceutically acceptable salt thereof, which may also contain pharmaceutically acceptable carriers, such as starches, sugars, and microcrystalline cellulose, diluents, granulating agents, lubricants, binders, disintegrating agents, and, optionally, other therapeutic ingredients. Because of the acid instability of the diazeniumdiolates, it is advantageous to coat oral solid dosage forms with an enteric or delayed-release coating to avoid release of the entire dose of nitric oxide in the stomach, unless the stomach is the therapeutic target organ.

A preferred method of coating the solid dosage form includes the use of non-aqueous processes to enteric or time-release coat the dosage form in order to reduce the likelihood that nitric oxide will be released from the dosage form during the coating process. These non-aqueous coating techniques are familiar to one skilled in the art, such as that described in U.S. Pat. No. 6,576,258. A time-release coating has been described in U.S. Pat. No. 5,811,121 that uses a alkaline aqueous solution to coat solid dosage forms. This coating process would also serve to preserve the levels of diazeniumdiolate in the dosage form, as the release of nitric oxide is drastically inhibited at higher pH levels.

Rectal and additional dosage forms can also be developed by a person skilled in the art, keeping in mind the acid instability of the diazeniumdiolate class of compounds and their sensitivity to aqueous solutions at neutral pH. One of ordinary skill in the art would be able to develop appropriate dosage forms on the basis of knowledge with excipients which are suitable for the desired pharmaceutical formulation.

EXAMPLES

The following examples further illustrate the present invention. Except where noted, all reagents and solvents are obtained from Aldrich Chemical Company (Milwaukee, Wis.). Nitric Oxide gas is supplied by Matheson Gas Products. A detailed description of the apparatus and techniques used to perform the reactions under an atmosphere of NO gas has been published (Hrabie et al., 1993) and is incorporated herein by reference in its entirety. The IR spectra are obtained on a Perkin Elmer 1600 series FTIR. Monitoring and quantification of the evolved NO gas is performed using a Thermo Environmental Instruments Model 42C NO—$NO_2$—NOx detector calibrated daily with a certified NO gas standard. The quantity of NO released is measured in parts per billion ppb, which is determined as follows: the NO-releasing material is placed in a chamber that has a steady stream on nitrogen gas flowing through it. The nitrogen is a carrier gas that serves to sweep any NO that is generated within the chamber into a detector. A measurement of 100 ppb means that 100 molecules of NO was generated for every billion of the nitrogen gas sweeping the chamber.

Example 1

This example provides a method to convert commercially available chloromethylated polystyrene into a carbon-based diazeniumdiolate including a nitrile group. A 50 ml aliquot of DMF is dried over sodium sulfate and then the pre-dried solvent is used to swell 2.37 g (4.42 mmol Cl per g) of chloromethylated polystyrene. After 30 minutes, 3.39 g (52 mmol) KCN and 0.241 g (1.4 mmol) of KI are added. The solution is heated to 60° C. overnight. During this time the resin changes from off white to brick red in color. The resin is washed consecutively with 20 ml portions of DMF, DMF:$H_2O$, $H_2O$, EtOH and $Et_2O$ and allowed to air dry. The disappearance of the —$CH_2$—Cl stretch at 1265 $cm^{-1}$ and appearance of the nitrile absorption at 2248 $cm^{-1}$ is indicative of substitution.

Diazeniumdiolation: In a Parr pressure vessel, the modified resin-CN is added to 20 ml DMF. This solution is slowly stirred and treated with 20 ml (20 mmol) of 1.0 M sodium trimethylsilanolate in THF. The vessel is degassed and charged with 54 psi NO gas. The head space is flushed with argon and the resin was washed with water, methanol and ether. The tan/slightly orange product was allowed to air dry. This method of diazeniumdiolation avoids the possibility of imidate formation that results when using an alkoxide as the base. This material provides a large burst of NO as shown in FIG. 1.

Example 2

This example provides a method to convert commercially available chloromethylated polystyrene into a carbon-based diazeniumdiolate including a —$OCH_3$ group.

To a 50 ml solution of 1:1 DMF/MeOH, the following are added: 1.0 g chloromethylated polystyrene (4.38 mmol Cl/g), 0.014 g KI (0.08 mmol), and 1.0 ml 25% NaOMe (4.37 mmol). The solution is stirred at room temperature overnight. It is then vacuum filtered and washed with MeOH and ether. The product's total weight of 1.0 g is slightly higher than the 0.979 g theoretical weight.

Diazeniumdiolation: The resin-$OCH_3$ is put in a Parr pressure vessel and 50 ml of 1:1 DMF/MeOH is added. While stirring, 2.0 ml 25% NaOMe (8.76 mmol) is added. The solution is degassed by alternating cycles of inert gas pressurization/venting before exposure to 50 psi NO gas. The consumption of NO gas, an indication of the reaction of the gas with the resin, is determined the next day. In one example, it was observed that 10 psi of NO gas was consumed. After vacuum filtration, washing and air drying, the weight gain is observed. Even in the absence of weight gain, the composition produced can have a positive Greiss reaction (See, Schmidt and Kelm, 1996 for Greiss reaction) as well as NO release, as detected by chemiluminescence.

Example 3

This example provides a method to convert commercially available chloromethylated polystyrene into a carbon-based diazeniumdiolate including an —$OC_2H_5$ group. To a 50 ml solution of 1:1 DMF/EtOH, the following are added: 1.0 g chloromethylated polystyrene (4.38 mmol Cl/g), 0.016 g KI (0.09 mmol), and 1.7 ml 24% KOEt (4.38 mmol). The solution is stirred overnight at room temperature. It is then vacuum filtered and washed with EtOH and ether. In one example, the observed weight was 1.22 g, which was slightly more than the expected 1.04 g.

Diazeniumdiolation: The resin-$OC_2H_5$ is placed in a Parr pressure vessel with 50 ml solution of 1:1 DMF/MeOH, and 2.0 ml of 25% NaOMe (8.76 mmol) is added. The vessel is degassed and exposed to 60 psi NO gas overnight. The resin is then washed with methanol and ether, and air dried. In one example, this material had a positive Greiss reaction and spontaneously generates NO under physiological conditions, as detected by an NO gas detector, shown in FIG. 2.

Example 4

This example provides a method to convert commercially available chloromethylated polystyrene into a carbon-based diazeniumdiolate including an —$SC_2H_5$ group.

In a fume hood, to 50 ml of dried DMF, the following are added: 1.00 g chloromethylated polystyrene (4.42 mmol Cl/g), 40 mg (0.24 mmol) potassium iodide and 372 mg (4.42 mmol) sodium ethanethiolate. This mixture is stirred at room temperature for 72 hours. It is filtered and washed with 25 ml portions of 1:1 DMF:MeOH, MeOH and $Et_2O$ and allowed to air dry.

Diazeniumdiolation: To one gram of resin-$SC_2H_5$ in a Parr pressure vessel, the following are added: 25 ml of THF and 2.0 ml (8.84 mmoles) of 25% sodium methoxide. The mixture is was degassed by alternating charging and discharging the pressure vessel with argon before exposure to 60 psi NO gas overnight. The resin is filtered and washed with 50 ml of 0.01M NaOH, ethanol and diethyl ether. The resulting resin produces a positive Greiss reaction. When measured in a chemiluminescent NO detector, 100 mg of resin produced $4.1 \times 10^{-11}$ moles NO/mg resin/min in pH 7.4 buffer at room temperature over a 1 hr period.

Example 5

This example provides a method to convert commercially available chloromethylated polystyrene into a carbon-based diazeniumdiolate including a —$OSi(CH_3)_3$ group. In 50 ml of dried DMF, the following are added: 1.00 g chloromethylated polystyrene (4.42 mmol Cl/g), 10 ml of 1.0 M (10 mmoles) sodium trimethylsilanolate and 100 mg (0.6 mmoles) potassium iodide. The mixture is heated to 100° C. for 24 hours. Thereafter, the resin is filtered and washed with 20 ml portions of DMF, MeOH and diethyl ether and allowed to dry in air.

Diazeniumdiolation: the following are placed in a Parr pressure vessel: 1.0 g of modified resin, 30 ml DMF and 2.0 ml (8.84 mmoles) 25% sodium methoxide. The pressure vessel is degassed and then exposed to 60 psi NO for 24 hours. The resin is then filtered and washed consecutively with DMF, MeOH and diethyl ether. Thereafter the resin is dried in air and produces a positive Greiss reaction. When measured in a chemiluminescent NO detector, 100 mg of resin produced $4.1 \times 10^{-11}$ moles NO/mg resin/min in pH 7.4 buffer at room temperature over a 40 min period.

Example 6

This example provides a method to convert commercially available chloromethylated polystyrene into a carbon-based diazeniumdiolate including a diethylamine group.

A 2.17 g sample of chloromethylated polystyrene (4.42 mmol Cl$^-$/g) is added to 50 ml of DMF. To this suspension, the following are added: 0.123 g (0.74 mmol) KI and 5 ml (72 mmol) diethylamine. The suspension is stirred at 45° C. for 24 hours and then filtered and washed twice with DMF, MeOH and ether. The resin is allowed to air dry.

Diazeniumdiolation: The following are added to a Parr pressure vessel: 100 ml MeOH, 1.0 g modified resin and 2.0 ml (8.7 mmol) 25% NaOMe. After degassing, the solution is exposed to 60 psi NO gas for 24 hours. The resin is then filtered and washed with methanol and ether and allowed to air dry. Over a 150 min period, 100 mg of resin produced $9.3 \times 10^{-11}$ moles NO/mg resin/min in pH 7.4 buffer at room temperature.

Example 7

This example demonstrates that the NO derived from the resin originates from NO donor groups attached to the resin and not to delocalized free NO gas molecules trapped in the interstitial spaces.

A general concern working with these materials is the possibility of NO becoming trapped in the interstitial spaces within the resin, which can skew the total amount of NO produced from the resin. As a control experiment, 0.50 g of Merrifield resin is placed in 40 ml of a 1:1 DMF/MeOH solution, degassed and exposed to 80 psi NO gas for 24 hours. The resin was then filtered, washed several times with MeOH, acetone and ether. After drying in air, a 50 mg sample was placed in 5 ml of Greiss reagent, which would immediately oxidize NO to nitrite and reveal the presence of any nitrite colorimetrically. The reagent did not turn the characteristic purple color indicative of the presence of nitrite. Therefore, the NO that is detected from the resin is due to the formation of NO donor groups and not to trapped NO.

Example 8

This example provides a method to convert a polymer containing an aromatic ring in the backbone of the polymer e.g. poly(ethylene terephthalate) (PET) into a carbon-based diazeniumdiolate.

In a 150 ml beaker, 2.0 g of PET pellets (Sigma-Aldrich, Milwaukee, Wis.) are treated with 10 ml of acetic acid and 10 ml of 37 wt % formaldehyde. The reaction is allowed to stir for 24 hours. The hydroxylated PET is then filtered and washed with three 25 ml portions of water and dried at 100° C. for one hour.

The hydroxylated PET is then suspended in 50 ml of pyridine, chilled in an ice bath, and treated with 4.67 g ($2.4 \times 10^{-2}$ mol) of p-toluenesulfonyl chloride. Two minutes after the addition of the p-toluenesulfonyl chloride the reaction is allowed to warm to room temperature. After twenty-four hours, the reaction is filtered and washed with two portions (25 ml) of dried DMF.

The tosylated PET is then placed in 25 ml of dried DMF and 2.03 g ($3.1 \times 10^{-2}$ mol) of KCN is added with gentle stirring. After twenty-four hours, the cyanomethylated PET is filtered and washed with DMF (25 ml), 1:1 DMF:$H_2O$ (25 ml), $H_2O$ (2×25 ml), and MeOH (2×25 ml).

The cyanomethylated PET is then placed in a 300 ml Parr pressure vessel to which 25 ml of MeOH is added. The suspension is gently stirred and 1.0 ml of a 1.0 M solution of sodium trimethylsilanolate in tetrahydrofuran is added to the suspension. The pressure vessel is purged and vented 10 times with argon and then charged with NO (80 psi). After twenty-four hours the diazeniumdiolated PET is filtered and washed with 25 ml of EtOH and 25 ml of $Et_2O$. The release characteristics for this compound are described in Example 14.

Example 9

In this example, a metal is coated with a siloxane and converted into an NO-releasing agent.

A piece of Nitinol, 5 mm×25 mm, is first polished with emery paper. It is then submersed in a oxidizing solution consisting of a 1:1 mixture of 1.0 M HCl and 30% $H_2O_2$ for 10 minutes. It is washed with water and acetone before blowing dry with argon. The clean, oxidized Nitinol strip is immersed in 6 ml of anhydrous hexadecane under an argon atmosphere. To this is added 0.2 ml dodecyltrichlorosilane, 0.2 ml chloromethylphenyltrichlorosilane and 50 µl of n-butylamine.

After 24 hours, the Nitinol strip is removed, dipped in ethanol to remove unbound particles and placed in an oven at 110° C. for 15 minutes to cure. The siloxane modified Nitinol strip is then placed in a round bottom flask containing 7 ml anhydrous hexadecane and heated to 80° C. To this is added 0.3 ml of chlorotrimethylsilane and this is allowed to react for 1 hour. The end-capped Nitinol strip is submerged in ethanol to remove any particles before drying at 110° C. for 20 minutes.

Next, the chloromethylphenylsiloxane Nitinol piece is placed in 15 ml of DMF, heated to 80° C. and 10 mg of potassium cyanide, 80 mg tetrabutylammonium bromide and several catalytic grains of potassium iodide are added. The reaction is allowed to progress overnight. The Nitinol strip is washed with ethanol before immersion in a Parr pressure vessel containing 50 ml DMF. To this is added 250 µl of sodium trimethylsilanolate. With gentle stirring, (avoid knocking the Nitinol strip) the vessel is degassed and exposed to 60 psi NO gas for 24 hours. The Nitinol piece is then washed with ethanol and ether and dried under argon gas. Submersion of a piece of Nitinol treated in this manner in Greiss reagent produces a positive reaction. The Nitinol piece becomes purple in color as liberated NO is oxidized to nitrite.

Example 10

In this example, silica gel is coated with a siloxane and converted into an NO-releasing agent. In 50 ml of toluene is placed 2.01 g of silica gel. The headspace is purged with argon. Then, 0.45 ml of chloromethylphenyltrichlorosilane is added. The suspension is gently stirred at room temperature overnight. The silica is then filtered and washed with toluene and air dried. The siloxane modified silica is then placed in 50 ml DMF and treated with 1.0 g KI and 1.0 g KCN. The temperature is then raised to 110° C. for 3 hours. The silica turns an dark off-red color during this phase. The silica is then filtered, washed with DMF, $H_2O$ and methanol. It is then oven dried at 110° C. for 20 minutes, and placed in a Parr pressure vessel with 50 ml THF. To this is added 2.0 ml of 1.0 M $NaOSi(CH_3)_3$. The vessel is degassed and exposed to 60 psi NO gas for 24 hours. The silica is filtered, washed with THF, MeOH and $Et_2O$ and allowed to air dry. The modified silica gel yields a positive Greiss reaction.

Example 11

In this example, the NO-releasing metal of Example 9 is treated with a protecting group to increase the duration of NO-release. A piece of Nitinol from Example 9 is submerged in a vial containing DMF. To this is added 50 µl of Sanger's Reagent; 2,4-dinitrofluorobenzene. The reaction is allowed to proceed at room temperature overnight. The next day the Nitinol piece is removed, washed with ethanol and dried in air.

Example 12

This example demonstrates the use of carbon-based diazeniumdiolate polymers in the ex vivo inhibition of human platelets. Blood is collected in 0.105 M sodium citrate vacutainers from healthy volunteers who have not consumed aspirin in the last 10 days or any NSAIDs (non-steroidal anti-inflammatory drugs) in the last 48 hours. Platelet rich plasma (PRP) is isolated by centrifuging whole citrated blood for 10 min at 2000 rpm in a Sorvall clinical centrifuge. Platelet poor plasma (PPP) is prepared by centrifuging PRP for 5 minutes at 7000 rpm in a microcentrifuge. PRP is maintained in a water bath at 37° C. with gentle shaking.

Aggregometry: 5.0 ml of PRP is placed in 14 ml polypropylene tubes and 20 mg/ml of the NO-releasing polymer is added. Platelets are incubated for 15 min at 37° C. with gentle shaking. 500 µl aliquots are placed in an aggregation cuvette and blanked against PPP in a Chronolog Aggregometer (37° C., 900 rpm). A baseline trace is taken for 1 min and 10 µl collagen (1 mg/ml) added. Aggro-link software (Chronolog) is used to calculate the % aggregation response after a 5 min trace. The results are tabulated as follows.

| Group | % aggregation |
| --- | --- |
| Control | 62.5 (50, 75) |
| Thioethyl polymer | 9.5 (7, 12) |
| Nitrile polymer | 15 |
| Ethoxy polymer | 42 |

Example 13

This example demonstrates the ability of carbon-based diazeniumdiolate polymers to reduce the level of pathogens in stored human platelets.

PediPak platelet storage containers are filled using sterile technique with 3 gm of cyano-modified chloromethylated polystyrene diazeniumdiolate from Example 1, and 2 gm of ethoxy-modified chloromethylated polystyrene diazeniumdiolate from Example 3, (Treated) or used as is (control). Platelets from a human platelet concentrate are added to each bag (25 ml per container) using a sterile connecting line. Each group is inoculated with 102 colony-forming units per ml (CFU/ml) of an overnight culture of S. epidermides. Aliquots from each group are immediately removed for assessment of CFU/ml. The platelets are then stored under the typical storage conditions of 22° C., with mild agitation. Twenty-four hours later, additional aliquots are removed for assessment of CFU/ml.

The CFU/ml is determined by serially diluting the aliquots with sterile broth, plating the dilutions onto sterile agar and counting the number of colonies that form on the plate after 24 hrs of incubation at 37° C. The results are tabulated as follows:

| Group | CFU/ml |
| --- | --- |
| Control | 5280 |
| Treated | 80 |

Example 14

This example shows the ability of a device comprised of a PET-derived carbon-based diazeniumdiolate polymer to add NO to a liquid flowing through the device.

An FPLC column of diameter 0.5 cm and length 10 cm is loaded with 1.2446 g of the carbon based diazeniumdiolate nitrile poly(ethylene terephthalate) from Example 8 (roughly estimated to have a surface area of 1914 $mm^2$/g). To ensure maximum packing the column is tapped while inserting the polymer.

The loaded column is attached to a length of Tygon tubing and 40 ml of 7.4 phosphate buffer is pumped through the column at a rate of 5 ml/min. One minute fractions are collected in 20 ml vials. Aliquots (0.5 ml) are removed from each fraction and assayed for nitrite (assaying nitrite is an excellent surrogate for measuring NO) using the Griess assay. One ml of Griess reagent is added to the fraction in a 3 ml cuvette and the absorbance is read at 546 nm. The results show an initial burst on NO in the first fraction, and a decreased but stable release of NO for the remaining fractions.

| Fraction # | µM NO released (measured as the oxidized product) |
|---|---|
| 1 | 101 |
| 2 | 12.5 |
| 3 | 7.3 |
| 4 | 5.4 |
| 5 | 6.1 |

Experiment 15

This example details an experiment used to study the effect of a device similar to that studied in Example 14 on a mammalian organ that has been isolated for preservation and/or transplantation, or an in vivo organ undergoing an ischemic event.

To study the effects of a device designed to deliver donorless NO on organ vascular tone, the organ is tested either in situ or isolated. The animals are anesthetized, heparinized, and an abdominal incision is made to expose the kidney. Both the renal artery and vein are cannulated and the organ is perfused with an oxygenated buffer using a peristaltic pump at a constant flow at 85 to 95 mmHg for approximately two hours. The system is monitored with flow gauges both proximal and distal to the organ and a pressure gauge proximal to the organ. The organ is perfused until the flow and pressure are stable. The flow circuit is then altered using two 3-way stopcocks to allow the perfusate to flow through a donorless NO releasing device. As the perfusate flows through the device and the effluent delivers the dissolved NO (technically NO.) to the organ, the blood vessels dilate resulting in recordable changes in the flow (increased) and pressure readings (decreased).

To study the effects of donorless NO delivery on organ oxidative state, an ischemic-reperfusion injury is created by ligating the renal pedicule with a tourniquet for 30 to 90 minutes. During this time the renal artery proximal to the ligature is cannulated and connected to a system that delivers a perfusate to the organ after the appropriate time point is reached. At the desired time-point, the tourniquet is removed, the renal vein severed, and the perfusate is pumped through the organ using a roller pump at a constant flow at 85 to 95 mmHg for approximately two hours. The renal cortical tissue is dissected away (as the effects of ischemia/reperfusion injuries are more pronounced at the level of the proximal tubule) and homogenized. The following antioxidant enzymes and cellular components are then measured: reduced glutathione, superoxide dismutase, catalase, glutathione peroxidase. Levels of these enzymes are known to be reduced with reperfusion injury (Dobashi et al., 2000). Protection from the oxidative damage caused by ischemia/reperfusion insult is indicated by statistically greater levels of the antioxidative enzyme panel above in the NO-treated group versus those levels in the control kidneys not receiving NO.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

Example 16

Preparation of a Contact Lens Case Made of Pet, Modified as Described in the instant specification and analysis of the its antimicrobial properties.

A standard contact lens case is manufactured using PET using the most appropriate method as known by one skilled in the art. The case is treated with acetic acid and 37% wt formaldehyde, as described in Example 8. The case is suspended in pyridine, chilled in an ice bath, and treated with at least 4.67 g of p-toluenesulfonyl chloride. Two minutes after the addition of the p-toluenesulfonyl chloride the reaction is allowed to warm to room temperature. After twenty-four hours, the contact lens case is removed and washed with two portions of dried DMF.

The tosylated PET is then placed in an appropriate volume of dried DMF and least 2.03 g ($3.1 \times 10^{-2}$ mol) of KCN is added with gentle stirring. After twenty-four hours, the cyanomethylated PET is filtered and washed with DMF, 1:1 DMF:$H_2O$, $H_2O$, and MeOH.

The cyanomethylated PET is then placed in a 300 ml Parr pressure vessel to which an appropriate volume of MeOH is added. The suspension is gently stirred and at least 1.0 ml of a 1.0 M solution of sodium trimethylsilanolate in tetrahydrofuran is added to the suspension. The pressure vessel is purged and vented 10 times with argon and then charged with NO (80 psi). After twenty-four hours the diazeniumdiolated PET contact lens case is removed and washed with sufficient amounts of EtOH and $Et_2O$.

Several diazeniumdiolated contact lens cases, and an equal number of control cases are were gassed with 80 psi nitrogen, instead of NO, and then challenged with a strain or strains of bacteria commonly found to contaminate contact lens cases including but not limited to *P. aeruginosa, S. aureus, S. epidermidis, Bacillus* spp., *Propionibacterium* spp., *Corynebacterium* spp., and *Mycobacterium* spp. After a 24 hour incubation period, the lens cases are rinsed gently three times in a mild buffer, and quantitatively assessed for the degree of bacterial colonization, such assessment including but not limited to scanning electron microscopy, removal of adhered bacteria by physical (sonication) or chemical (detergent removal) means, and/or counting microorganisms by microscopy or spectophotometry, as known to those of skill in the art. The antimicrobial effect of the diazeniumdiolated contact lens cases is indicated by a statistically significant decrease in the amount of adhered bacteria versus the amount found on the control contact lens cases.

Experiment 17

Analysis of the resistance of NO-releasing surfaces to the formation of viable microbial biofilms. Glass disks (5 mm) are coated with a siloxane-based NO-releasing polymer of the present invention. Control disks are coated but gassed with nitrogen instead of NO. The diazeniumdiolated and control disks are placed in the wells of 96 well microtiter plate where bacterial biofilms are then grown as described previously (Yarwood et al. 2004; Hasset et al. 1999; Pitts et al. 2003). Overnight cultures of bacteria in Tryptic Soy Broth (TSB) (or species specific medium) are diluted 1:10 in sterile TSB. The 96 well plates are coated with Fetal Calf Serum, and washed twice with PBS, in order to create a conditioning film. Subsequently, wells are filled with 180 µl sterile TSB. Wells are then inoculated with 20 µl of the suspension of the bacteria under study. The plates are incubated at 37° C. for 24 hours. Planktonic cells and medium are removed by aspiration after which the wells are washed twice with sterile PBS.

Viability of the cells comprising the biofilm is assayed as described previously (Pitts et al. 2003) with minor adjustments. 100 µl prewarmed PBS containing 1% glucose, 0.5 µg/ml 13-(4,5-dimethyl-2-thiazolyl)-2,5-diphenyl-2H-tetrazolium bromide (MTT) (5 mg/ml stock in PBS, store in aliquots at −20° C.), 1 µM menadione (from 1 mM stock in acetone) is added to each well. The plates are incubated statically at 37° C. for 1 hour, after which the wells are aspirated. Then, 100 µl acid isopropanol (5% 1N HCl) is added to dissolve the formazan crystals. The plates are incubated at ambient temperature for 10 min while shaking. The solution is then transferred to clean 96 well plates and the absorbance at 550 nm is determined utilizing a spectrophotometric plate reader to measure the number of metabolically active bacteria in the biofilm.

A statistically significant decrease in the absorbance readings at 550 nm in the wells containing NO-releasing disk coatings versus the control disk coatings indicates a reduction in viability of the biofilm. Similar experiments are performed with fungal biofilms and mixed bacterial/fungal biofilms.

Example 18

The resistance of NO-releasing surfaces to platelet adhesion. Glass coverslips are coated using the same procedure as described in Example 10. Control coverslips are gassed with nitrogen instead of NO. Control and NO-releasing slides are sealed into a flow cell mounted on the stage of a fluorescent microscope with a video recording camera and whole human blood is circulated through the cell at 37° C. under high shear conditions (1000 s-1), and fluorescence is monitored. Deposition of platelets to the surface is indicated by white fluorescent spots on the video image. Experiments are controlled such that the same blood donor is tested using NO-releasing and control coatings. An effective antiplatelet coating is indicated by zero fluorescence with less than 5% area coverage for the NO-releasing coating versus a strong fluorescent image, with greater than 20% area coverage for the control coatings.

Example 19

Demonstration of the ability of NO-releasing coatings to enhance the growth of endothelial cells on artificial surfaces. Glass slides are coated with a nitrile-modified (see Example 1) siloxane diazeniumdiolate monolayer polymer (similar to Example 9), or the identical polymer that is gassed with nitrogen instead of NO (as control that does not release NO). Slides are sterilized in alkalinized 70% ethanol for at least 20 min. The slides are placed in respective sterile Petri dishes. C166 bovine endothelial cells are seeded in the Petri dishes at $1 \times 10^4$ cells/ml, using 4 malls. The samples are incubated at 37° C. under 5% $CO_2$. After 24 hours, the number of endothelial cells adhering to the coated slide is counted by the following method. The slides are transferred to fresh Petri dishes where the cells are released from the slide using EDTA and trypsinization extraction, followed by washing, staining, centrifugation to concentrate the cells, and counting using a hemocytometer. These experiments demonstrate the ability of an NO-releasing coating to accelerate the endothelialization of a foreign surface.

| Coating Group | Cells per ml of extract |
|---|---|
| Control | $2.7 \times 10^5$ |
| NO-releasing | $1.3 \times 10^6$ |

Example 20

Evaluation of a cardiovascular stent coated with an NO-releasing coating as described in the instant application. A stent is coated as described in the present invention. The stents are implanted using the porcine coronary artery restenosis model according to the guidelines and procedures of Schwartz and Edelman, 2002. Three experimental groups including an NO-releasing coated stent, a non-NO-releasing coated stent (i.e. coated but not exposed to NO gas according to the present invention), and a plain metal stent, are implanted into animals treated with antiplatelet medication (aspirin and clopidogrel, 24 hrs pre surgery and continuing). Stents with a stent:artery ratio of 1.0 to 1.1 are used. The implantation of the stents is performed under anesthesia. Stented arteries, approximately 10 per experimental group, are evaluated at 7 days, 28 days, and 3 months.

Efficacy of the NO-releasing coating is determined by the absence of thrombi and a statistically significant reduction of neointimal growth compared to bare stents, using the quantitative and semi-quantitative methods described in Schwartz and Edelman.

The invention claimed is:

1. A composition comprising a carbon-based diazeniumdiolate compound attached to at least one phenyl-containing polymer, and having the formula:

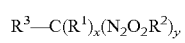

wherein x is an integer from 0 to 2 and y is an integer from 1 to 3, and the sum of x plus y equals 3;
wherein $R^1$ is not an imidate or thioimidate;
wherein $R^2$ is selected from the group consisting of a countercation and a protecting group on the terminal oxygen; and
wherein $R^3$ is a phenyl of said phenyl-containing polymer.

2. A composition comprising a carbon-based diazeniumdiolate compound attached to at least one phenyl-containing polymer that comprises a polymer backbone, wherein the phenyl of said phenyl-containing polymer is pendant from the backbone of said polymer, and wherein said composition has the following general formula:

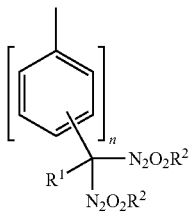

wherein R¹ not an imidate or thioimidate; and wherein R² is selected from the group consisting of a countercation and a protecting group on the terminal oxygen.

3. A medical device coating comprising a nitric oxide-releasing polymer, wherein said nitric oxide-releasing polymer comprises the composition of claim 1.

4. The medical device coating of claim 3, wherein said medical device is selected from the group consisting of a vascular stent, a vascular graft, a catheter, a wound a bandage, a blood collection bag, a blood component storage bag, an extracorporeal membrane oxygenation (ECMO) circuit, an internal monitoring device, an external monitoring device, and a device that comes in contact with mammalian tissue in vivo, in vitro, or ex vivo.

5. A medical device, wherein all or part of the device comprises a nitric oxide-releasing polymer that comprises the composition of claim 1.

6. The composition of claim 1, wherein the at least one phenyl-containing polymer comprises one or more polystyrene units cross-linked with divinylbenzene.

7. The composition of claim 2, wherein the at least one phenyl-containing polymer comprises one or more polystyrene units cross-linked with divinylbenzene.

8. A medical device coating comprising a nitric oxide-releasing polymer, wherein said nitric oxide-releasing polymer comprises the composition of claim 2.

9. The medical device coating of claim 8, wherein said medical device is selected from the group consisting of a vascular stent, a vascular graft, a catheter, a wound dressing, a bandage, a blood collection bag, a blood component storage bag, an extracorporeal membrane oxygenation (ECMO) circuit, an internal monitoring device, an external monitoring device, and a device that comes in contact with mammalian tissue in vivo, in vitro, or ex vivo.

10. A medical device, wherein all or part of the device comprises a nitric oxide-releasing polymer that comprises the composition of claim 2.

11. The composition of claim 6, wherein R¹ is selected from the group consisting of a cyano group; an ether group, a tertiary amine, and a thioether.

12. The composition of claim 7, wherein R¹ is selected from the group consisting of a cyano group; an ether group, a tertiary amine, and a thioether.

13. The composition of claim 6, wherein R¹ is a cyano group.

14. The composition of claim 7, wherein R¹ is a cyano group.

15. The composition of claim 6, wherein the carbon-based diazeniumdiolate compound attached to at least one phenyl-containing polymer comprises the following moiety:

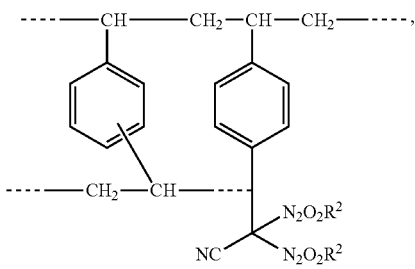

wherein R² is a countercation.

16. The composition of claim 15, wherein R² is Na.

17. A medical device coating comprising a nitric oxide-releasing polymer, wherein said nitric oxide-releasing polymer is the composition of claim 15.

18. The medical device coating of claim 17, wherein said medical device is selected from the group consisting of a vascular stent, a vascular graft, a catheter, a wound dressing, a bandage, a blood collection bag, a blood component storage bag, an extracorporeal membrane oxygenation (ECMO) circuit, an internal monitoring device, an external monitoring device, and a device that comes in contact with mammalian tissue in vivo, in vitro, or ex vivo.

19. A medical device, wherein all or part of the device comprises a nitric oxide-releasing polymer that comprises the composition of claim 15.

20. A system for localized release of nitric oxide to a target site, the system comprising:

the composition of claim 6;

whereby decomposition of a carbon-bound diazeniumdiolate moiety to produce nitric oxide occurs under physiological conditions and does not produce a nitrosamine donor molecule.

* * * * *